US005718903A

United States Patent [19]
Adams et al.

[11] Patent Number: 5,718,903
[45] Date of Patent: Feb. 17, 1998

[54] **VACCINE COMPRISING *BRUCELLA ABORTUS* WHICH HAS O POLYSACCHARIDE ANTIGEN ABSENT**

[75] Inventors: Leslie Garry Adams; Richard P. Crawford; Donald S. Davis; Thomas A. Ficht; Roger Smith, III, all of College Station; Blair A. Sowa, Bryan; Joe W. Templeton; John D. Williams, both of College Station, all of Tex.; Albert M. Wu, Tao-yuan, Taiwan

[73] Assignee: The Texas A&M University System, College Station, Tex.

[21] Appl. No.: 196,777

[22] Filed: Feb. 14, 1994

Related U.S. Application Data

[63] Continuation of Ser. No. 841,616, Feb. 25, 1992, abandoned, which is a continuation-in-part of Ser. No. 320,912, Mar. 7, 1989, abandoned, which is a continuation of Ser. No. 32,183, Mar. 30, 1987, abandoned.

[51] Int. Cl.$^6$ .............................. A61K 39/10; C12N 1/21
[52] U.S. Cl. .................................. 424/235.1; 424/197.11; 424/252.1; 424/823; 435/252.1; 435/822; 530/350; 530/352; 530/359
[58] Field of Search .................... 424/235.1, 197.11, 424/252.1, 823; 435/252.1, 822; 530/350, 352, 359

[56] References Cited

U.S. PATENT DOCUMENTS

| | | |
|---|---|---|
| 2,787,576 | 4/1957 | Kakavas . |
| 4,402,939 | 9/1983 | Fournier . |
| 4,831,126 | 5/1989 | Bundle . |
| 5,006,463 | 4/1991 | Cherwonagrowdzky ............... 424/92 |
| 5,023,174 | 6/1991 | Mayfield . |

FOREIGN PATENT DOCUMENTS 1352125  5/1974  United Kingdom .

OTHER PUBLICATIONS

Edwards et al., "A Study of the Immunological Properties and Infectivity of *Brucella abortus* Strain 45/20, McEwen, in Cattle," Vet. Rec. 57:259–265 (1945).
McEwen, A., "Further Experiments on the Infectivity of Vaccine Prepared From *Brucella abortus* Strain 45(20) for Cattle," Vet. Rec. 58:3–6 (1946).
Ficht et al, "Cloning the Genes Encoding the Major Outer Membrane Protein Omp III of *Brucella abortus* vaccine and virulent strains", DNA, 5 : 92, 1986.
Lutkenhaus, "Role of a Major Outer Membrane Protein in *Escherichia coli*", J. of Bact., 2: 631–637, 1977.
Sowa et al, "Physiology of F–Pilin Synthesis and Utilization", J. of Bact., 153:962–968, 1983.
O'Farrell, "High Resolution Two–Dimensional Electrophoresis of Proteins", J. of Bio. Chem., 250: 4007–4021, 1975.
Hunkapiller et al, "Isolation of Microgram Quantities of Proteins from Polyacrylamide Gels for Amino Acid Sequence Analysis", Meth. in Enz., 91: 227–236, 1983.

Alton et al, "Laboratory Techniques in Bruccellosis", World Health Org. Monograph Series (2d Ed.), 55: 11–63, 1975.
Young et al, "Construction of Genomic Libraries in Bacteriophage Vectors", Const. of Gen. Lib., 270: 270–294, (no year listed).
Young et al, "Efficient Isolation of Genes by Using Antibody Probes", Proc. Natl. Acad. Sci. USA, 80: 1194–1198, 1983.
Smith, "Recovery of DNA from Gels", Meth. in Enz., 65: 371–380, 1980.
Young et al, "Yeast RNA Polymerase II Genes: Isolation with Antibody Proves", Science, 222: 778–782, (no year listed).
Schuurs et al, "Enzyme–Immunoassay", Clinica Chimica Acta, 81: 1–40, 1977.
Towbin et al, "Electrophoretic transfer of proteins from polyacrylamide gels to nitrocellulose sheets: Procedure and some applications", Proc. Natl. Acad. Sci. USA, 76: 4350–4354, 1979.
Craven et al, "Purification, Composition, and Molecular Weight of the B–Galactosidase of *Escherichia coli* K12", J. of Biol. Chem., 240:2468–2477, 1965.
Alton et al, "Laboratory Techniques in Brucellosis", World Health Org., Monograph series, (2d Ed.), 64–66, 1975.
Southern, "Detection of Specific Sequences Among DNA Fragments Separated by Gel Electrophoresis", J. Mol. Biol., 98:503–517, 1975.
Mackett et al, "General Method for Production and Selection of Infectious Vaccinia Virus Recombinants Expressing Foreign Genes", J. of Virol., 49: 857–864, 1984.
Hopp et al, "Prediction of protein antigenic determinants from amino acid sequences", Proc. Natl. Acad. Sci. USA, 78: 3824–3828, 1981.
Kyte et al, "A Simple Method for Displaying the Hydropathic Character of a Protein", J. Mol. Biol., 157: 105–132, 1982.
Chou et al, "Prediction of the Secondary Structure of Proteins from their Amino Acid Sequence", Advances in Enzymology, 47: 45–148, 1978.
Merrifield, "Solid Phase Peptide Synthesis. I. The Synthesis of a Tetrapeptide", J. Amer. Chem. Soc., 85: 2149–2154, 1963.
Maniatis et al, "Construction of Genomic Libraries, Molecular Cloning", A Laboratory Manual, 270–294, 1982.
Bosseray, "Immunity to Brucella in mice vaccinated with a fraction (F8) or a killed vaccine (H38) with or without adjuvant level and duration of immunity in relation to dose of vaccine, recall injection and age of mice", Br. J. Exp. Path., 59: 354–365, 1978.

(List continued on next page.)

*Primary Examiner*—Anthony C. Caputa
*Attorney, Agent, or Firm*—Arnold, White & Durkee

[57] ABSTRACT

The present invention is an improved vaccine against *Brucella abortus* which permits differentiation between vaccinated and field strain infected cattle. The vaccine can be administered in two different forms: (1) cell envelopes isolated from an O polysaccharide antigen deficient, stable transposon mutant of *B. abortus* or (2) an O polysaccharide antigen deficient, stable transposon mutant of *B. abortus*.

7 Claims, No Drawings

OTHER PUBLICATIONS

Bosseray et al, "Antagonism between two immunogens extracted from Brucella (cell wall peptidoglycan and lipopolysaccharide fractions) and inactivity of the brucellin allergen in immunization of the mouse", *Ann. Microbiol.*, (Inst. Pasteus), 131A: 157–169, 1980.

Baldwin et al, "Immune response of cattle to *Brucella abortus* outer membrane proteins measured by Lymphocyte", *Veterinary Immunology and Immunopathology*, 9: 383–396, 1985.

Adams et al, "Analysis of *Brucella abortus* Antigens by Use of Monoclonal Antibodies, Sodium Dodecyl Sulfate–Polyacrylamide Gel Electrophoresis (SDS–PAGE), and Two–Dimensional Gel Electrophoresis, Repro. and Teratology", *Amr. College of Vet. Path.* (thirty–sixth annual meeting) & Amer. Soc. for Vet. Clinical Path. (third annual meeting) Dec. 9–13, 1985.

Winter et al, "Immune Response to Porin in Cattle Immunized with Whole Cell, Outer Membrane, and Outer Membrane Protein Antigens of *Brucella abortus* Combined with Trehalose Dimycolate and Muramyl Dipeptide Adjuvants", *Infection and Immunity*, 42: 1159–1167, 1983.

Cunningham et al, "The Use of Killed 45/20 Adjuvant Vaccine as a Diagnostic Agent in the Final Stages of the Eradication of Brucellosis: The Clearance of Brucellosis from Problem Herds by Interpretation of Anamnestic Serological Responses", *Vet. Rec.*, 89: 680–686, 1971.

Cunningham et al, "Vaccination of Cattle with Killed 45/20 Adjuvant Vaccine, Effects on Serological and Milk Ring Tests when used in cattle Previously Exposed to Infection or Vaccinated with S.19", *Vet. Rec.*, 86: 2–7, 1970.

Diaz et al, "The Immuno–diffusion Method for the Identification of Cattle Vaccinated with *Brucella abortus* Strain 45/20", *Vet. Rec.*, 93: 300–302, 1973.

Hall et al, "Infection and Serological Responses in Cattle given 45/20 Vaccine and Later Challenged with *Brucella abortus*", *Australian Vet. J.*, 52: 409–413, 1976.

Miller et al, "A complement fixation method for quantitative differentiation of reactions to 45/20 vaccine and brucella infection", *Vet. Rec.*, 98: 210–215, 1976.

Sutherland et al, "The Effect of Challenge with Virulent *Brucella abortus* on Beef Cattle Vaccinated as Calves or Adults with Either *Brucella abortus* Strain 19 or 45/20", *Australian Vet. J.*, 57: 470–473, 1981.

Waghela, "Serological response to cattle, sheep and goats in Kenya vaccinated with killed *Brucella melitensis* strain H38 adjuvant vaccine", *Vet. Rec.*, 112: 476–479, 1983.

Smith and Heffron, "Transposon Tn5 Mutagenesis of *Brucella abortus*", *Infection and Immunity*, 55: 2774–2776, 1987.

Harmon et al, "Survival of rough and smooth strains of *Brucella abortus* in bovine mammary gland macrophages", *Am. J. Vet. Res.*, 49: 1092–1097, 1988.

Feinberg and Volgelstein, "A technique of radiolabeling DNA Restriction Endonuclease fragments to high specific activity", *Analytical Biochemistry*, 132: 6–13, 1983.

Smith et al, "Measurement of Protein Using Bicinchoninic Acid", *Analytical Biochemistry*, 150: 76–85, 1985.

Kleckner, "Transposable elements in prokaryotes", *Ann. Rev. Genet.*, 15: 341–404.

Sowa et al, "Size, charge and structural heterogeneity of *Brucella abortus* lipopolysaccharides demonstrated by two–dimensional gel electrophoresis", *Electrophoresis*, 7: 283–288, 1986.

Plava and Makela, "Lipopolysaccharide heterogeneity in *Salmonella typhimurium* analyzed by sodium dodecyul sulfate–polyacrylamide gel electrophoresis", *Eur. J. Biochem.*, 107: 137–143, 1980.

Moreno et al, "Immunochemical characterization of Brucella lipopolysaccharides and polysaccharides", *Infect. Immun.*, 31:214–222, 1981.

Montaraz et al, "Protection against *Brucella abortus* in Mice with O–polysaccharide-specific monoclonal antibodies", *Infect. Immun.*, 51: 961–963, 1986.

Moreno et al, "Characterization of a native polysaccharide hapten from *Brucella melitensis*", *Infect. Immun.*, 55: 2850–2853, 1987.

Bundle et al, "Characterization of brucella polysaccharide B.", *Infect. Immun.*, 56: 1101–1106, 1988.

Price et al, "Ability of mononuclear phagocytes from cattle naturally resistant or susceptible to brucellosis to control in vitro intracellular survival of *Brucella abortus*", *Infect. Immun.*, 58: 879–886, 1990.

Moreno et al, "Purification and characterization of smooth and rough lipopolysaccharides from *Brucella abortus*", *J. Bacteriol.*, 138: 361–369, 1979.

McEwen and Roberts, "Bovine Contagious Abortion, the Use of Guinea–Pigs in Immunisation Studies", *J. Comp. Pathol. Ther.*, 49: 97–117, 1936.

Berg et al, "Transposable Kanamycin–Neomycin Resistance Determinants", *Microbiology*, American Society for Microbiology, Washington, D.C., 13–16, 1978.

Taylor, "Bactericidal and Bacteriolytic Activity of Serum Against Gram–Negative Bacteria", *Microbiol. Rev.*, 47: 46–83, 1983.

Jorgensen et al, "A restriction enzymen cleavage map of Tn5 and location of a region encoding neomycin resistance", *Mol. Gen. Genet.*, 177: 65–72, 1979.

Laemmli, "Cleavage of structural proteins during assembly of bacteriophage $T_4$", *Nature* (London), 227: 680–685, 1970.

Price et al, "Survival of smooth, rough and transposon mutant strains of *Brucella abortus* in bovine mammary macrophages", *Vet. Immunol. Immunopath.*, 26: 353–365, 1990.

McEwen, "The Virulence of *Br. abortus* for Laboratory Animals and Pregnant Cattle", *Vet. Rec.*, 52: 97–106, 1940.

Sowa et al, "SDS–soluble and peptidoglycan–bound proteins in the outer membrane–peptidoglycan complex of *Brucella abortus*", *Vet. Microbiol.*, 27: 351–369, 1991.

Schurig et al, "Biological properties of RB51; a stable rough strain of *Brucella abortus*", *Vet. Microbiol.*, 28: 171–188, 1991.

Bundle et al, "The lipopolysaccharide of *B. abortus* and *B. melitensis*", *Ann. Inst. Pasteur Microbiol.*, 38: 92–98, 1978.

Moriera–Jacob, "In vitro species (or type) transformation among strains of Brucella", *Nature*, 197: 406, 1963.

Ray, et al, "JB45/20 Vaccination in Brucella Infected Herd", *Proc. US Animal Health Assoc.*, 78:88–103, 1974.

Ewalt, et al, "Atypical isolates of *Brucella abortus* from Canada and the United States Characterized as Dye Sensitive with M Antigen Dominant", *Journal of Clinical Microbiology*, 25:698–701, 1987.

Lutkenhaus, "Role of a major outer membrane protein in *Escherichia coli*", *Journal of Bacteriology*, 131: 631–637, 1977.

Alton, et al, "Laboratory Techniques in Brucellosis", *World Health Organization*, Geneva, Chap. 1: 11–63, 1975.

Sanborn, et al, "Cloning and expression of *Brucella-abortus* outer membrane protein genes in *Escherichia coli*", *Abstracts of the Annual Meeting of the American Society for Microbiology*, 87: no 0, 80, 1987.

Sowa, "Membrane Proteins of Brucella spp.", Chapter 6, 85–105, In *Advances in Brucellosis Research*, Texas A&M University Press, L. Garry Adams, Ed., 1990.

Wu, et al, "Immunochemical and partial chemical characterization of fractions of membrane–bound smooth lipopolysaccharide–protein complex from *Brucella abortus*", *Molecular and Cellular Biochemistry*, 75:93–102, 1987.

Wu, et al. "Structural and immunochemical characterization of the O–haptens of *Brucella abortus* lipopolysaccharides from strains 19 and 2308", *Molecular and Cellular Biochemistry*, 75: 103–111, 1987.

Mayfield, et al, "The cloning, expression, and nucleotide sequence of a gene coding for an immunogenic *Brucella abortus* protein", *Gene*, 63: 1–9, 1988.

Alton et al, "Laboratory Techniques in Bruccellosis", *World Health Org. Monograph Series* (2d Ed.), 55: 40–70, 1975.

Verstreate, et al, "Outer membrane proteins of *Brucella abortus*: isolation and characterization", *Infection and Immunity*, 35:979–989, 1982.

Perry, et al, "Lipopolysaccharide Antigens and Carbohydrates of Brucella", Chapter 5, 76–88, In *Advances in Brucellosis Research*, Texas A&M University Press, L. Garry Adams, Ed., 1990.

L. Garry Adams, "Development of Live Brucella Vaccines", Chapter 17, 250–270, In *Advances in Brucellosis Research*, Texas A&M University Press, L. Garry Adams, Ed., 1990.

Halling, et al, "Deletion of the BSCP31 Gene of *Brucella abortus* by Replacement", *Infection and Immunity*, 59: 3863–3868, 1991.

Smith, et al, "Immunogenicity of Subcellular Fractions of *Brucella abortus*: Measurement by In Vitro Lymphocyte Proliferative Responses", *Veterinary Immunology and Immunopathology*, 25: 83–97, 1990.

Smith, et al, "Induction of lymphocyte responsiveness by the outer membrane–peptidoglycan complex of rough strains of *Brucella abortus*", *Veterinary Immunology and Immunopathology*, 26: 31–48, 1990.

Sangari, et al, "Mutagenesis of *Brucella abortus*: comparative efficiency of three transposon delivery systems", *Microbial Pathogenesis*, 11: 443–446, 1991.

Lai, et al, "Electroporation of a suicide plasmid bearing a transposon into *Brucella abortus*", *Microbial Pathogenesis*, 9: 363–368, 1990.

Douglas, et al, "Porins of Brucella species", *Infection and Immunity*, 44: 16–21, 1984.

Verstreate, et al, "Comparison of SDS–PAGE profiles and antigenic relatedness among outer membrane proteins of 49 *B. abortus* strains", *Infection and Immunity*, 46: 182–187, 1984.

Ficht, "A 36–KD *B. abortus* cell envelope protein is encoded by repeated sequences closely linked in the genomic DNA", *Infection and Immunity*, 56: 2036–2046, 1988.

Smith et al. American Journal of Veterinary Research 51 (4):512–517 (see abstract) Mar. 1991.

Corbeil et al. Infection and Immunity 56(12):3251–3261 (see abstract) Dec. 1988.

Santos et al, Infection and Immunity, vol. 46, No. 1, pp. 188–194 (Oct. 1984).

VACCINE COMPRISING *BRUCELLA ABORTUS* WHICH HAS O POLYSACCHARIDE ANTIGEN ABSENT

This application is a continuation of application Ser. No. 07/841,616 filed Feb. 25, 1992 (now abandoned), which is a continuation-in-part application of Ser. No. 07/320,912 filed Mar. 7, 1989, now abandoned, and which is a continuation of Ser. No. 07/032,183 filed Mar. 30, 1987, now abandoned.

The government may own certain rights in the present invention pursuant to USDA/SEA/ARS Cooperative Agreement No. 58-6125-5-4.

BACKGROUND OF THE INVENTION

1. Field of Invention

The present invention relates to an improved vaccine against *Brucella abortus*. Specifically, the invention is a novel vaccine in which specific antigens of *Brucella abortus* induce an immunological response which provides protective immunity yet permits differentiation between field strain infected and vaccinated cattle. This novel vaccine is made from either an O polysaccharide antigen deficient transposon mutant of *B. abortus* or from cell envelopes isolated from such a transposon mutant.

2. Description of the Related Art

*Brucella abortus* are gram-negative coccobacilli that affect the reproductive system of cattle. The organism is a facultative intracellular parasite capable of causing spontaneous abortion, reduced milk production, delayed conception in cows and sterility in bulls. Brucellosis in humans and laboratory animals does not ordinarily involve the reproductive system. In these cases systemic dissemination of the organism occurs mainly through the blood to the reticuloendothelial system organs. The immunological response of the host can stop and reverse this invasive process. However, the ability of this organism to invade and survive within host macrophages compromises the ability of the host immune system to completely eliminate infection. This frequently results in the recurrence of infection with consequences identical to primary infection.

Stimulation of a protective immune response in cattle is achieved by vaccination with the live attenuated vaccine *B. abortus* strain 19, however, complete characterization of the mechanism of protective immunity has not been performed. Primary focus has been placed on the outer membrane components including lipopolysaccharide (LPS or O polysaccharide antigen), native hapten, polysaccharide B and outer membrane proteins (OMPs) (Bundle, D. R., J. W. Chenwonogrodzky, M. Caroff and M. B. Perry. 1978. The lipopolysaccharide of *B. abortus* and *B. melitensis*. Ann. Inst. Pasteur Microbiol. 38:92–98; Bundle, D. R., J. W. Chenwonogrodzky, and M. B. Perry. 1988. Characterization of brucella polysaccharide B. Infect. Immun. 56:1101–1106; Moreno, E., H. Mayer, and I. Moriyon. 1987. Characterization of a native polysaccharide hapten from *Brucella melitensis*. Infect. Immun. 55:2850–2853; Moreno, E., M. W. Pitt, L. M. Jones, G. G. Schurig and O. T. Bermann. 1979. Purification and characterization of smooth and rough lipopolysaccharides from *Brucella abortus*. J. Bacteriol. 138:3361–369; Moreno, E., L. S. Speth, L. M. Jones and D. T. Berman. 1981. Immunochemical characterization of Brucella lipopolysaccharides and polysaccharides. Infect. Immun. 31:214–222). LPS consists of an hydrophobic lipid A region, the oligosaccharide core and the O-polysaccharide side chain which gives the cell surface its hydrophilic character. Native hapten which has recently been identified as the O-polysaccharide (Moreno, E., H. Mayer, and I. Moriyon. 1987. Characterization of a native polysaccharide hapten from *Brucella melitensis*. Infect. Immun. 55:2850–2853) and polysaccharide B is a complex mixture of low molecular weight glucans (Bundle, D. R., J. W. Chenwonogrodzky, and M. B. Perry. 1988. Characterization of brucella polysaccharide B. Infect. Immun. 56:1101–1106). Of these components, the O-polysaccharide side chain of the LPS is the most antigenic and has been shown to elicit a protective immune response in the mouse model (Montaraz, J. A., A. J. Winter, D. M. Hunter, B. A. Sowa, A. M. Wu, and L. G. Adams. 1986. Protection against *Brucella abortus* in Mice with O-polysaccharide-specific monoclonal antibodies. Infect. Immun. 51:961–963). However, it has also been demonstrated that the presence of LPS increases intracellular survival, presumably by blocking or actively inhibiting macrophage function (Harmon, D. G., L. G. Adams, and M. Frey. 1988. Survival of rough and smooth strains of *Brucella abortus* in bovine mammary gland macrophages. Am. J. Vet. Res. 49:1092–1097; Price, R. E., J. W. Templeton, and L. G. Adams. 1990. Survival of smooth, rough and transposon mutant strains of *Brucella abortus* in bovine mammary macrophages. Vet. Immunol. Immunopath. 26:353–365; Price, R. E., J. W. Templeton, R. Smith III, and L. G. Adams. 1990. Ability of mononuclear phagocytes from cattle naturally resistant or susceptible to brucellosis to control in vitro intracellular survival of *Brucella abortus*. Infect Immun. 58:879–886).

To reduce the incidence and economic loss caused by bovine brucellosis, several different vaccines have been used in the past. The vaccines are generally prepared using either live or killed strains of Brucella. The most common of these is strain 19. The use of these vaccines has several disadvantages. One disadvantage is that currently there is no consistently effective means for distinguishing strain 19 vaccinated cattle from those infected by pathogenic strains of *Brucella abortus*. Both the vaccine and the pathogenic strain cause the production of cross-reacting antibodies which serve as the basis for current serological tests for brucellosis.

Other disadvantages of some of the killed vaccines include: the need to inject the vaccine twice; the instability of several of the strains used to create the vaccines; the vaccines frequently cause large tissue reactions at the site of injection; the immunity induced is also short lived; and the protective immunity is suboptimal.

Crude protein derivatives have also been used experimentally to produce protective immunity. These crude extracts have the same disadvantages as the killed and live vaccines. Additionally, the extracts are crude and contain cellular components not required to induce protective immunity. This can cause further confusion in differentiating between vaccinated and field strain infected cattle.

In the early 1920's McEwen (McEwen, A. D., R. S. Roberts. Bovine contagious abortion. The use of guinea-pigs in immunization studies. J. Comp. Pathol. Ther. 1936, 49:97–117) isolated smooth *B. abortus* strain 45 from cattle which demonstrated to be relatively avirulent yet stimulate protective immunity in guinea pigs. While attempting to restore virulence to strain 45 by serial passage through guinea pigs, McEwen (McEwen, A. D. The virulence of *B. abortus* for laboratory animals and pregnant cattle. Vet. Rec. 1940; 52:97–106) discovered that the 20th guinea pig passage of *B. abortus* strain 45, i.e. strain 45/20, conferred protective immunity; however, when live strain 45/20 was injected into pregnant cows, it reverted to smooth pathogenic form that resulted in infection, abortion, and production of smooth agglutinins. Taylor and McDiarmid (Taylor, P. W. Bactericidal and bacteriolytic activity of serum against gram-negative bacteria. *Microbiol. Rev.* 1983; 47:46–83) later compared intravenous injections of strain 45/20 and strain 19 in pregnant cows which demonstrated that clinical 45/20 and strain 19 in pregnant cows which demonstrated that clinical disease was caused by smooth revertants of strain 45/20 which required higher $CO_2$ for primary isolation. Additionally, whole cells of strain 45/20 combined with an adjuvant (K45/20A) have been used in cattle as a killed vaccine, but questionable protection and sporadic reversion of the organism to the smooth form during commercial fermentation often resulted in agglutination and complement fixation titers indistinguishable from field strain infection thereby, greatly reducing the use of this organism as effective vaccine (Ray, W C and Hendricks, J B. 45/20 Vaccination in a Brucella Infected Herd, *Proc. Ann. Meeting USAHA*, 78:88–103, 1974).

The instant invention claims a vaccine which provides protective immunity against pathogenic *Brucella abortus* and permits differentiation between vaccinated and field strain infected cattle.

SUMMARY OF THE INVENTION

The present invention is an improved vaccine against *Brucella abortus* which permits differentiation between vaccinated and field strain infected cattle. The vaccine can be administered in two different forms: (1) cell envelopes isolated from an O polysaccharide antigen deficient, stable transposon mutant of *B. abortus* or (2) an O polysaccharide antigen deficient, stable transposon mutant of *B. abortus*.

One embodiment of this invention is a vaccine for providing protective immunity to a host animal against pathogenic *Brucella abortus*. This vaccine comprises cell envelopes isolated from an O polysaccharide antigen deficient, stable transposon mutant of *B. abortus*, in an amount sufficient to induce protective immunity, together with a suitable carrier, wherein said cell envelopes contain intrinsic antigens of *B. abortus* except O polysaccharide antigen.

The Applicants prefer isolating cell envelopes from the exemplary O polysaccharide antigen deficient, stable transposon mutant of *B. abortus*, 2308 m106 R::Tn5lacZ, having ATCC Accession No. 67912.

A further aspect of this invention is the vaccine comprising cell envelopes isolated from an O polysaccharide antigen deficient, stable transposon mutant of *B. abortus*, wherein said amount of cell envelopes ranges from about 400 µg to about 4000 µg.

Another embodiment of this invention is the above vaccine further comprising a suitable adjuvant. There are a variety of different adjuvants that would be suitable for the claimed vaccine and known to those skilled in the art. However, the Applicants prefer employing an adjuvant consisting essentially of 0.25 milligrams monophosphoryl lipid A, 0.25 milligrams *Mycobacterium spp.* cell wall skeleton, 0.25 milligrams of trehalose dimycolate, 120 milligrams of lecithin, 0.1 milliliters DRAKEOL 6VR™ mineral oil and 0.004 milliliters of TWEEN 80™ monooleate detergent.

More specifically, the claimed vaccine for providing protective immunity to a host animal against pathogenic *Brucella abortus* comprises cell envelopes isolated from an O polysaccharide antigen deficient, stable transposon mutant of *B. abortus*, in an amount ranging from about 400 µg to about 4000 µg, together with a suitable carrier, and these cell envelopes of the claimed vaccine contain intrinsic antigens of *B. abortus* except O polysaccharide antigen.

There are a variety of different methods known to those skilled in this art for killing the stable transposon mutant of the claimed invention. However, the Applicants prefer to employ exposure of the transposon mutant to a sufficient dose of $^{60}$Cobalt radiation at 4° C. to render the stable transposon mutant nonviable. Nonviability is tested by standard methods known to those skilled in this art.

Another preferred aspect of the claimed invention is the method for isolating cell envelopes from the killed transposon mutants. The Applicants prefer the methods described in detail in the specification. This procedure preserves intrinsic antigens of *B. abortus*.

Another embodiment of this invention are cell envelopes isolated from an O polysaccharide antigen deficient, stable transposon mutant of *B. abortus* that contain intrinsic antigens of *B. abortus* except O polysaccharide antigen. An exemplary source for these cell envelopes is the O polysaccharide antigen deficient stable transposon mutant of *B. abortus*, 2308 m106 R::Tn5lacZ, having ATCC Accession No. 67912.

A further embodiment of this invention is a vaccine for providing protective immunity in a host animal against pathogenic *Brucella abortus* comprising an O polysaccharide antigen deficient, stable transposon mutant of *B. abortus*, in an amount sufficient to induce protective immunity. More specifically, this O polysaccharide antigen deficient, stable transposon mutant of *B. abortus* further contains intrinsic antigens of *B. abortus* except O polysaccharide antigen. For the claimed invention, the preferred amount of stable transposon mutant ranges from about $10^9$ to about $10^{11}$ colony forming units. Additionally, an exemplary source of this stable transposon mutant is *B. abortus* 2308 m106 R::Tn5lacZ having ATCC Accession No. 67912. Another aspect of the instant invention is the O polysaccharide antigen deficient, stable transposon mutant of *B. abortus* is further attenuated.

Yet another embodiment of this invention is an O polysaccharide antigen deficient, stable transposon mutant of *Brucella abortus*, wherein this transposon mutant contains intrinsic antigens of *B. abortus* except O polysaccharide antigen. An exemplary source of an O polysaccharide antigen deficient, stable transposon mutant of *Brucella abortus* is *B. abortus* 2308 m106 R::Tn5lacZ, having ATCC Accession No. 67912.

Vaccines comprising cell envelopes from O polysaccharide antigen deficient, stable transposon mutants of *B. abortus* have the additional advantages of sterile immunity and nonpathogenicity to humans and animals. Therefore, individuals other than certified veterinarians can use the vaccines safely.

The use of live O polysaccharide antigen deficient, stable transposon mutants of *B. abortus* have the advantage of providing longer-lived immunity than killed bacteria.

DETAILED DESCRIPTION OF THE PREFERRED EMBODIMENTS

As noted above, the immunizing agent of the present invention can be in two forms. The following is a discussion of the preferred methods which can be used to create the different immunizing agents of this invention. It will be obvious to those skilled in the art that deviations from the procedures discussed below are possible without departing from the basic scope of the invention.

EXAMPLE I

Methods Employed for Production of Vaccines against *Brucella abortus*

This example details the methods employed for vaccine production against *Brucella abortus*.

A. Sources and Microorganisms Used for Production of Non-viable Subunit Vaccine Against B. Abortus

1. Source

*Brucella abortus* Strain 19, and *Brucella abortus* Strain 2308 were kindly provided by Dr. Billy Deyoe (USDA/ARS/NADC, Ames, Iowa) and Strain 2308 M106 was produced by following the protocol set forth below.

2. Microorganisms

*Brucella abortus* Strain 19 and *Brucella abortus* Strain 2308 were maintained on potato infusion agar (PIA) plates and were grown to confluency on trypticase soy agar (TSA) plates for 48 hours at 37° C. in an atmosphere of air containing 5% $CO_2$. Growth from each plate was harvested into 5 ml of peptone saline (1% Bacto-peptone, 0.5% NaCl) before use.

A transposon mutant of strain 2308 *Brucella abortus* was isolated using the technique as described below. This transposon mutant, identified as *Brucella abortus* 2308 R::Tn5lacZ (m106), was deposited Mar. 27, 1989 with the American Type Culture Collection 12301 Parklawn Drive, Rockville Md. 20852 and assigned ATCC Deposit No. 67912. This transposon mutant lacks O polysaccharide antigen common to smooth strains of *Brucella abortus*.

Cell envelopes isolated from m106 transposon mutant has been used as an immunizing agent to create a *Brucella abortus* vaccine which provides protective immunity, yet still permits differentiation between field strain infected and vaccinated cattle (Data presented in Example III).

The live transposon mutant m106 is currently being used as an immunizing agent to create a *Brucella abortus* vaccine which provides protective immunity, yet still permits differentiation between field strain infected and vaccinated cattle. This study with the live transposon mutant m106 is similar to the current practice using strain 19.

3. Production and Characterization of Transposon Mutants Vaccine Strains of *Brucella abortus* Strain 2308

(a) Introduction

A method for producing immunizing agents against *Brucella abortus* which induces an immunological reaction against *Brucella abortus* and still permits differentiation between vaccinated and field strain infected cattle was achieved through the development of transposon mutants. The mutants were developed through P1 and Mu phage infections of *Brucella abortus*. The methods employed utilized the capacity of the broad range bacteriophage P1 of *Escherichia coli* to deliver the transposon to *B. abortus* S2308 via mating with *E. coli* carrying the broad range plasmid derivative of RK2 (Smith, L. D., and F. Heffron. 1987. Transposon Tn5 mutagenesis of *Brucella abortus*. Infect. Immun. 55:2774–2776). Smith and Heffron suggested that P1 infection preferentially selects rough-cell variants which arise spontaneously in in vitro cultures due to increased surface for attachment.

(b) Methods for Producing Transposon Mutants

P1 and Mu phages were isolated from *E. coli* SF800 P1::Tn5 lacZ $kan^R$ and $str^S$ and *E. coli* CT151 $kan^R$ $str^S$. The *E. coli* CT151 contains the lysogenic bacteriophage Mu::TnS(d1) $kan^R$ and $str^S$. The strains were isolated by streaking them out on LB (10 g BACTO-TRYPTONE™ nutrient, 5 g yeast extract, 5 g NaCl, pHed to 7.5) plates containing 40 micrograms/milliliters of kanamycin sulfate. The plates were then incubated at 30° C. for 24 hours. A single colony was selected and used to inoculate a 50 milliliter culture of LB broth containing 40 micrograms/milliliters of kanamycin sulfate. The flasks were incubated overnight with a gentle agitation at 30° C. The overnight culture was used to inoculate 500 milliliters of LB broth containing 5 mM $CaCl_2$. LB broth which was not pHed was used to avoid calcium precipitation. $CaCl_2$ was also required for the CT151 strain growth.

The cultures were grown to an $OD_{600}$ of 0.4 and then rapidly warmed to 42° C. by immersing the cultures in a 90° C. water bath. The temperature was monitored using an ethanol rinsed thermometer. The culture flasks were placed in an air shaker and vigorously aerated at 42° C. for 30 minutes and then cooled to a temperature of 38° C. The vigorous aeration was continued for approximately 90 minutes or until the cells were lysed. Temperatures was maintained above 37° C. during this process to ensure that sufficient lysis occurs. Following lysis, the cultures were adjusted to 2% in $CHCl_3$ and agitated an additional 10 minutes to ensure complete lysis.

The cell supernatant was then adjusted to 0.5M in NaCl and chilled to 4° C. The supernatant was kept at that temperature for at least 60 minutes. Bacterial debris was removed by centrifugation at 8000 rpm for 10 minutes. To ensure increased stability of the Mu bacteriophage, the following salts were added: 1–3 mM $MgSO_4$ and 1–3 mM $Pb(OAc)_2$. Solid polyethylene glycol 8000 (PEG) was added to a final concentration of 10% (w/v) and the solution was incubated at 4° C. for at least 60 minutes. The PEG precipitate was pelleted by centrifugation at 8000 rpm for 20 minutes. The pellet containing bacteriophage was resuspended in an ice cold P1 buffer (10 mM Tris-HCl, pH 7.6, 10 mM $CaCl_2$) or Mu buffer (10 mM Tris-HCl, pH 7.6, 1 mM $MgSO_4$, 1 mM $Pb(OAc)_2$) at 1/50 the original volume and kept on ice. For each 3.5 milliliters of resuspended PEG pellet, 2.4 grams of solid CsCl was added and the resulting solution was centrifuged to equilibrium for 24 hours in an 8 OTi rotor at 38,000 rpm at a temperature of 5° C. The bacteriophage bands were located by their opacity using a high intensity lamp and collected by side puncture of the tubes. The harvested bacteriophage were dialyzed against three changes of 500 milliliters of P1 and Mu buffers and stored at 4° C. over $CHCl_3$.

(1) Infection of *Brucella abortus* With P1 and Mu Phage

A confluent plate of *Brucella abortus* S-2308 was incubated for 48 hours at 37° C. on potato infusion agar (PIA) or trypticase soy agar (TSA). The cells were then harvested from the plate into 5 milliliters of non-pHed tryptose broth adjusted to 10 mM $CaCl_2$. The S-2308 cell suspension was diluted 100-fold prior to infection. To the tube containing the 1:100 dilution of the S-19 cells, 0.1 milliliters of the phage prepared as described above was added and incubated without agitation at 38° C. for 30 minutes. The reaction was diluted two-fold with 1.0 milliliters of non-pHed tryptose broth (without $CaCl_2$). The solution was transferred to a screw cap jar in a shaking water bath at a temperature of 38° C. The mixture was incubated for 2 hours with vigorous agitation. Following the shaking, 0.4 milliliter aliquotes were spread onto PIA or TSA plates containing 25–40 micrograms/milliliters of kanamycin. The plates were incubated at 38° C. Negative controls without bacteriophage were used in the experiment. The plates were checked beginning at day 3 and for as long as 14 days. Any colonies observed were picked and restreaked for isolation. Colonies so isolated were characterized as outlined below (Alton, *Laboratory Techniques in Brucellosis*, World Health Organization, Geneva 64–66 (1975). Stock suspensions were stored in 50% glycerol at −70° C.

(c) Identification of Transposon Mutant Genotype

1) DNA isolation

To identify the genetic lesion caused by transposon mutagenesis, hybridization analysis using Tn5 DNA as a hybridization probe was performed as described by Southern, *J. Mol. Biol.*, 98:503–517 (1975).

Briefly, genomic DNA from *B. abortus* was isolated by a rapid mini-prep method of lysis and restriction enzyme digestion. A confluent plate of *B. abortus* containing $1 \times 10^{11}$ cells was harvested in 5 ml of phenol saline (0.85% NaCl, 0.5% Phenol) heat killed at 80° C. for at least 1 hour. The cells were then pelleted by centrifugation at 5000 xg, and washed once with 5 ml of buffer A (10 mM Tris-HCl (pH 7.6), 1M NaCl), and resuspended in buffer A prewarmed to 42° C. at a final concentration of 100 mg/ml(wet wt.) of cells.

The cells suspension was then mixed with an equal volume of a 42° C. solution of 1.5% low melting point agarose in sterile, distilled water. The mixture was then molded in blocks (approximate volume 50–100 μl). Each block was then incubated in lysis buffer (6 mM Tris-HCl (pH 7.6), 1M NaCl, 100 mM EDTA(pH 7.5), 0.5% SARKO-SYL™ detergent (wt/vol.), 0.5% BRIJ-58™ surfactant (vol/vol) (available from ICI Americas, Inc.), and 0.2% deoxycholate (wt/vol.; filter sterilized) containing 1 mg/ml lysozyme and 20 μg/ml RNase A overnight at 37° C. The lysing buffer was aspirated and the block incubated for 72 hours at 50° C. in ESP buffer (0.5M EDTA (pH 9.5), 1% SDS and 2 mg/ml proteinase K). The buffer was aspirated and the block incubated for 2–4 hours in high salt buffer with 10 mM Phenylmethylsulfonyl fluoride (PMSF) at room temperature, followed by an incubation in high salt buffer with β-mercaptoethanol (Biorad) at room temperature overnight.

The plug was washed in two changes of sterile distilled water and melted in 0.5 ml of sterile distilled water at 70° C. for 10 minutes, cooled to 37° C. DNA digestion was performed according to the specification of the manufacturer (Boehringer, Mannheim, Biochemicals, Indianapolis, Ind.). Electrophoretic separation of the fragments was then performed on 0.7% wt/vol. horizontal agarose gel (Maniatis, T. E., F. Fritsch, and J. Sambrook. 1982. *Molecular cloning: a laboratory manual*. Gold Spring Harbor Laboratory, Cold Spring Harbor, N.Y.). Bacteriophage lambda DNA was digested with HindIII and used as molecular weight marker. Plasmid pDJ13 containing Tn5 which codes for kanamycin resistance gene, was purified from *E. coli* MM294 by CsCl gradient centrifugation. The vector P1 phage was purified from *E. coli* MM294 (Miller, J. H. 1972. *Experiments in molecular genetics*. Cold Spring Harbor Laboratory, Cold Spring Harbor, N.Y.) and prepared by CsCl gradient centrifugation.

2) Electrophoresis of DNA and Hybridization reactions

Genomic or plasmid restriction fragments were separated on the basis of size by agarose gel electrophoresis and ethidium bromide staining as described by Maniatis. The transfer of DNA to nylon filters (Zeta-probe, Bio-Rad Lab., Richmond, Calif.) was a modification of the technique of Southern (Southern, E. M. 1975. Detection of specific sequences among DNA fragments separated by gel electrophoresis. *J. Mol. Biol.* 98:503–517). Filters were prehybridized with 30 ml buffer (1.5 XSSPE, 1.0% wt/vol. SDS, 0.5% wt/vol. Blotto, 100 μg/ml denatured salmon sperm DNA) for 16 hours at 68° C. DNA was probed with either a 12 kb Bam HI-HindIII fragment constructed in pBR322 and containing P1::Tn5lacZ or a 3.3 kb HindIII fragment isolated from pDJ13 that contains the gene encoding neomycin phosphotransferase II. Radioactive labeling of these DNA fragments to high specific activity was carried out as described by Feinberg and Volgestein (Feinberg, A. P. and B. Volgelstein. 1983. A technique of radiolabeling DNA Restriction Endonuclease fragments to high specific activity. *Analytical Biochemistry*, 132:6–13). The filter was then exposed to Kodak XAR-5 X-ray film. The autoradiograms were developed after 1–24 hours of incubation at −70° C.

3) SDS-Polyacrylamide gel electrophoresis

One dimensional gel analysis was performed on bacterial whole cell lysates and cell envelope preparations of *B. abortus* as described by Sowa, et al (Sowa, B. A., R. P. Crawford, F. C. Heck, J. D. Williams, A. M. Wu, K. A. Kelly, L. G. Adams. 1986. Size, charge and structural heterogeneity of *Brucella abortus* lipopolysaccharides demonstrated by two-dimensional gel electrophoresis. *Electrophoresis*, 7:283–28). *B. abortus* S19 and mutants were grown on tryptose agar plates and suspended in phosphate buffered saline. Radiation killed *B. abortus* cells were centrifuged and pellets were solubilized in Laemmli sample buffer (2% SDS, 4% 2-B-mercaptoethanol, 10% glycerol, 1M Tris-HCl (pH 6.8), and 0.1% bromophenol blue) and heated at 100° C. for 10 minutes. Whole cell lysates and cell envelopes were subjected to SDS-PAGE using the Laemmli buffer system (Laemmli, U.K. 1970. Cleavage of structural proteins during assembly of bacteriophage $T_4$. Nature (London), 227:680–685) with a 4% (w/v) stacking gel and 12.5% (w/v) separating gel. Phosphorylase b (94,000 molecular weight), bovine serum albumin (68,000 M.W), ovalbumin (43,000 M.W.) carbonic anhydrase (30,000 M.W), soybean trypsin inhibitor (21,000 M.W), and lysozyme (14,300 M.W) from Bio-Rad Laboratories were used as molecular mass standards. Gels were either stained with COOMASSIE™ dye blue R-250 (Sigma Chemical Co.) or were silver stained, using the Bio-Rad silver stain kit. Stained gels were then photographed without drying.

(d) Characterization Studies of Transposon Mutant A mutant form of strain 2308 *Brucella abortus* has been created using the above technique and is identified as *Brucella abortus* 2308 R::Tn5lacZ (m106). This transposon mutant has been deposited with the American Type Culture Collection and been assigned ATCC Deposit No. 67912. Specific characteristics of this mutant were analyzed and are presented below.

1) Isolation of kanamycin-resistant *B. abortus* mutants

Bacteriophage P1 carrying Tn5lacZ, was able to infect *B. abortus*, which is normally sensitive to kanamycin, resulting in insertion mutants that were kanamycin resistant (kant). These kan$^r$ insertion mutants arose at a frequency of transfer between $1–5 \times 10^{-10}$ per infected cell.

Over 100 stable insertion mutants selected on TSA agar supplemented with kanamycin have been isolated. Using this method all mutants were resistant to 40 μg/ml of kanamycin sulfate suggesting that these *B. abortus* mutants are not spontaneous mutants, and they all produced β-galactosidase because the transposon contain the lacZ gene. They were also sensitive to 5 μg/ml of streptomycin sulfate suggesting that streptomycin resistance encoded by Tn5 is not expressed in *B. abortus*. Similar observations were reported by Smith and Heffron.

Characterization of these independent insertion mutants were performed using classical biotyping in order to confirm their identity as *B. abortus* and to isolate mutants with peculiar phenotype traits.

2) DNA Analyses of Transposon Mutants of *B. abortus*

Southern blot hybridization of DNA restriction fragments demonstrated that a single copy of Tn5 was inserted into the genomic DNA of mutants.

Genomic DNA was prepared and digested with several restriction endonucleases. The DNA restriction fragments were separated by electrophoresis and transferred to nylon (Zeta-Bind) by Southern blotting. There is one EcoRI, one HindIII and BamHI site in Tn5lacZ (Berg, D. E., R. Joregensen, and J. Davies. 1978. Transposable kanamycin-neomycin resistance determinants. In *Microbiology*—1978 (ed. D. Schlessinger), p. 13. American Society for Microbiology, Washington, D.C.; Jorgensen, R. A., S. J., Rothstein, and W. S. Rezuikoff. 1979. A restriction enzyme cleavage map of Tn5 and location of a region encoding neomycin resistance. *Mol. Gen. Genet.* 177:65), therefore digestion of genomic DNA by EcoRI, HindIII or BamHI should yield two DNA fragments that contain the left and right portions of Tn5lacZ for each site of insertion. When the 12 kb Bam HI-HindIII fragment was used as a probe, two bands were observed.

To ensure that the mutant contained only Tn5lacZ and was not a lysogen of P1, Southern hybridization was repeated with P1 phage DNA. The mutants failed to form hybrids with DNA from Phage P1 (data not shown). Because sequences homologous to Tn5lacZ are not present in the control strain 19 and kanamycin resistant insertion mutants do not contain P1 DNA sequences, it is evident that the mutants acquired Tn5lacZ by P1::Tn5lacZ infection followed by transposition of Tn5lacZ from the phage P1 vector and by loss of the P1 vector from the lineage.

These data indicated the isolation of a Brucella transposon mutant which exhibited characteristics of rough O polysaccharide deficient strain and retained the properties of the parent strain 2308. Removal of the transposon has not been possible either in vivo or in vitro.

To decipher the structure of the LPS responsible for the atypical behavior of the mutant cell envelopes was characterized using SDS-polyacrylamide gel electrophoresis. LPS polymers can be dissociated into subunits by the detergent action of SDS and its mobility has been shown to be dependent on molecular size rather than intrinsic charge (Plava, E. T. and P. H. Makela. 1980. Lipopolysaccharide heterogeneity in *Salmonella typhimurium* analyzed by sodium dodecyl sulfate-polyacrylamide gel electrophoresis. *Eur. J. Biochem.* 107:137–143; Sowa, et al., *Electrophoresis,* 7:283–288, 1986).

3) One Dimensional SDS-PAGE of Transposon Mutants of *B. abortus*

Silver staining of cell envelope preparations from smooth and rough strains of Brucella and the mutant on 12.5% polyacrylamide gels demonstrated that each LPS entity gives a single somewhat diffuse band of characteristic mobility. The smooth strain *B. abortus* 2308 showed a set of bands which appeared as a broad diffuse band when stained with silver. The pattern of the bands of rough strain 45/20 were fast migrating but reverts to the smooth form after animal passage. The mutant, S2308 M106::Tn5LaCZ was stable and demonstrated no detectable bands.

4) Monoclonal Binding to Transposon Mutants of *B. abortus*

Monoclonal anti-O-antigen antibody (Montaraz, J. A., Winter, A. J., Hunter, D. M., Sowa, B. A., Wu, A. M., Adams, L. G., Protection Against *Brucella abortus* in mice with O-polysaccharide specific monoclonal antibodies, *Infection and Immunity,* 51:961–963, 1986; Sowa, et al, *Electrophoresis,* 7:283–288, 1986) reacted with immunoblots of SDS-PAGE of cell envelopes from strain 2308 with the typical multiple bands of LPS. Antibody reactivity was present in the high molecular weight region of the gel and reactivity was absent at the low molecular weight region of the gel. Inhibition tests performed with purified O-antigen established that the O-antigen is a perosamine homopolymer (1,2 linked 4, 6 dideoxy-4-formamido-1-D-mannose) by nuclear resonance analysis. Competitive inhibition assays of immunoblots demonstrated that 10 μg of purified O-antigen inhibited a 1:200 dilution of the O-antigen specific monoclonal antibody. In addition, competitive inhibition ELISA (Montaraz, J. A., A. J. Winter, D. M. Hunter, B. A. Sowa, A. M. Wu, and L. G. Adams. 1986. Protection against *Brucella abortus* in Mice with O-polysaccharide-specific monoclonal antibodies. *Infect. Immun.* 51:961–963) performed with soluble strain 19 antigen demonstrated that purified O-antigen inhibited the monoclonal antibody by 86%.

In contrast, S2308 M106::Tn5LacZ did not react with O-antigen specific monoclonal antibody. The lack of reactivity of this antibody with this transposon mutant strain is consistent with the absence of O polysaccharide antigen.

B. METHODS EMPLOYED FOR MAINTAINING CULTURES

1. Maintenance and Identification

*B. abortus* cultures were maintained and identified by the techniques described in *Laboratory Techniques in Brucellosis* G. G. Alton, L. M. Jones, and D. E. Pietz, World Health Organization, Geneva, 1975, page 11–63. The *B. abortus* strain 2308 m106 transposon mutant was maintained in kanamycin sulfate containing medium.

2. Virulence and Purity of Cultures

Purity of *B. abortus* was maintained as given in Alton, Jones and Pietz (see reference above) with continual surveillance of colonial morphology by direct observation, crystal violet staining and biotyping for characteristics of the genus Brucella.

Virulence of Strain 19 was determined by inoculation of non-vaccinated pregnant first calf heifers by subcutaneous injection of $1\times10^9$ CFU and observing the heifers through a normal parturition.

Strain 2308 virulence was determined by conjunctival instillation of $1\times10^7$ CFU and observation for the effects on pregnancy which usually results in greater than 70% abortion with culture positive results from the fetal, placental and maternal tissues at parturition and necropsy. Strain 2308 M106 was non-pathogenic for pregnant goats (data presented in Example II).

3. Composition and Reaction of Media

The media used for *B. abortus* was prepared as follows:

| | |
|---|---|
| Bacto-dextrose | 30.0 g |
| peptone "M" | 30.0 g |
| Bacto-yeast extract | 10.0 g |
| sodium dihydrogen phosphates | 9.0 g |
| disodium hydrogen phosphate (anhydrous) | 3.3 g |
| distilled water | 1 liter |

While mixing, the water was brought just to boiling and peptone "M" was added. The solution was allowed to simmer for 15 minutes and then allowed to cool for 10 minutes. While mixing, dextrose, yeast extract, sodium dihydrogen phosphate, and disodium hydrogen phosphate are then added. The solution was cooled for about 30 minutes, the pH (about 6.4) was checked and the 800 ml of medium was filtered into the 1 liter fermentation flask. The hose was removed from the medium inlet port and the port was immediately covered with cotton saturated with 70% ethanol. The sterile cap was removed from the beaker and placed on the medium inlet port of the fermentation flask containing 10 ml of distilled water and 0.4 ml of anti-foam 60 silicone emulsion.

Bacto-dextrose and Bacto-yeast extract were obtained from Difco Labs, Detroit, Mich., peptone "M" was obtained from Pfizer Diagnostics Division, Chas. Pfizer & Co., New York, N.Y., sodium dihydrogen phosphates were obtained from Merck & Co., Inc., Rahway, N.J.

4. Character, Size, and Shape of Container

*B. abortus* cultures were grown in a 1 liter cylindrical Asti Scientific Zworts Co. fermentation flask with computer controllable pH, $CO_2$, and temperature.

5. Storage Conditions of Seed Cultures

An ampoule of dried *B. abortus* seed was reconstituted with distilled water. This dried *B. abortus* seed was used to inoculate a number of potato agar slopes contained in tubes that were at least 20×150 mm in size and were placed at an angle while the medium was hardening so that the sloped surface of the medium is at least 50 mm long.

The inoculated slopes were incubated for 48 hours and used to seed production cultures. The seed slopes were stored in the refrigerator at 4° C.; generally they were stored for as long as 2–3 months before being used to seed production cultures.

6. Methods of Preparing Suspensions for Seeding or Inoculation

*B. abortus* organisms were grown on potato agar which had uniform smooth colony characteristics as determined by crystal-violet staining for Strain 2308. Consistently rough 2308 M106 colonies are suspended in peptone-saline solution for enumeration of organisms in the suspension by serial-dilution plate counts.

7. Technique of Inoculating Seed and Production Media

Seed cultures of *B. abortus* were removed from the 4° C. refrigerator or from the −20° freezer, warmed to room temperature and resuspended with sterile peptone-saline solution. Appropriate serial dilutions were made and duplicate potato agar plates were inoculated uniformly to quantitate the number of colony forming units/ml.

$1 \times 10^{11}$ CFU/ml of either Strain 19, 2308 or 2308 M106 in peptone-saline solution were inoculated into the 1 liter fermentation flask as described above.

8. Conditions and Times for Incubation

The fermentation flask was inoculated with at least $1 \times 10^{11}$ CFU of *B. abortus* Strain 19, 2308 or 2308 M106 obtained by harvesting a 48-hour growth from a seed slope. Once inoculated, the fermentation flask was incubated at 37° C. for 48 hours using the following rates for agitation and aeration.

After 48 hours incubation, a sample was removed for examination and the brucellae were removed from the medium by centrifuging at 5000× g.

| Incubation time in (hours) | Air flow rate (liters/min) | Agitation rate (rev/min) |
|---|---|---|
| 0–8 | 4 | 300 |
| 8–24 | 6 | 400 |
| 24–32 | 8 | 500 |
| 32–48 | 10 | 600 |

9. Character and Amount of Growth

Examinations were carried out on the fermentation sample and the satisfactory results for *B. abortus* are as follows:

| viable count | $2.5–3 \times 10^{11}$ per ml |
|---|---|
| pH | 7.2–7.4 |
| density (packed cell volume) | 8–9% |
| purity | 100% brucellae |
| dissociation | none |

10. Method of Killing

Harvested thick paste-like sediment of all *B. abortus* was placed in 50 ml polycarbonate Oakridge tubes and frozen at −20° C. The frozen suspension of bacteria were subsequently irradiated at a total dosage of 1.38 megarads using a $^{60}Co$ industrial gamma radiation source. Verification of inactivation was confirmed by culture of 0.2 ml of the treated cultures on TSA in 5% carbon dioxide with incubation at 37° C. for 5 days.

C. Harvest

1. Composition and Reaction of Media

The following recipe was used for *B. abortus:*

| Bacto-dextrose | 30.0 g |
|---|---|
| peptone "M" | 30.0 g |
| Bacto-yeast extract | 10.0 g |
| sodium dihydrogen phosphates | 9.0 g |
| disodium hydrogen phosphate | 3.3 g |
| distilled water | 1 liter |

While mixing, the water was brought just to boiling and peptone "M" was added. The solution was allowed to simmer for 15 minutes, and then allowed to cool for 10 minutes.

While mixing, dextrose, yeast extract, sodium dihydrogen phosphate, and disodium hydrogen phosphate were added. The solution was cooled for about 30 minutes, the pH (about 6.4) was checked and the 800 ml of medium was filtered into the 1 liter fermentation flask. The hose was removed from the medium inlet port and the port was immediately covered with cotton saturated with 70% ethanol. The sterile cap was removed from the beaker and placed on the medium inlet port of the fermentation flask containing 10 ml of distilled water and 0.4 ml of anti-foam 60 silicone emulsion.

2. Minimum and Maximum Period of Time From Inoculation Until Harvest

Time from inoculation until harvest was 48 hours ±2 hours for *B. abortus.*

3. Technique of Harvesting

Following fermentation, the medium containing *B. abortus* was immediately (i.e. no more than 5 minutes) harvested by centrifugation at 5000× g in a refrigerated centrifuge at 4° C. The supernatant was aspirated from the sediment while collecting the supernatant in a trap filtration flask.

4. Specification for Acceptable Harvest Material

Examinations were carried out on the fermentation sample and the satisfactory results for *B. abortus* were as follows:

| viable count | $2.5–3 \times 10^{11}$ per ml |
|---|---|
| pH | 7.2–7.4 |
| density | 8–9% |
| purity | 100% brucellae |
| dissociation | none |

5. Handling of Discarded Material

All supernatant and discarded material from *B. abortus* cultures were autoclaved for 15 minutes at 15 psi at 121° C.

Preparation of Vaccine Against *B. Abortus*

1. Method of Inactivation

Refer to Method of Killing (see #10 above) for details.

2. Composition of Adjuvant

Each individual 10-dose vial for cattle contained the following lyophilized adjuvant mixture:

1) 2.5 mg Monophosphoryl lipid A
2) 2.5 mg Trehalose dimycolate
3) 2.5 mg Cell Wall Skeleton 4) 1.0 ml Drakeol 6VR 5) 0.04 ml Monooleate (Tween 80)

6) 1200 mg Lecithin

3. Method and Degree of Concentration of Cell Envelopes

Cell envelopes from *B. abortus* Strain 2308 M106 were prepared as follows. Cultures of *Brucella abortus* strain S2308 M106 were fermenter grown in Trypticase soy broth to an $OD_{550}$ of 106–133. The cells were harvested, rendered nonviable by irradiation with 1.38 Mrad of $^{60}Co$ gamma radiation at 4° C., and frozen at –20° C. The cells were then thawed and subjected to osmotic and sonic shock to rupture the cells and purified cell envelopes were collected by the method described by J. F. Lutkenhaus, *J. Bacteriol.*, 131:631–637 (1977), with the following modifications: 10 milliliter aliquots of thawed suspended cells were centrifuged at 12,000 rpm (10,000 x g) for 5 minutes at 4° C. to remove the cells from suspension. The resulting supernatant was then discarded. The pelleted cells were resuspended in 12 milliliters of Lutkenhaus buffer and subjected to 20,000 Hz sonic disruption for 6 consecutive periods of both 3 minutes at 300 watts and 2 minutes at 50 watts of power. During the sonication process, the suspension was held in an ice bath. The suspension was centrifuged at 12,000 rpm for 5 minutes to remove any unlysed cells and the resulting pellet was discarded. (Sowa, B. A., et al, *Veterinary Microbiology*, 27:351–369 (1991)). The supernatant from above was centrifuged at 30,000 rpm (100,000× g) at 4° C. for 45 minutes and the resulting supernatant was discarded. The pellets were resuspended in 1.5 milliliters of Lutkenhaus buffer by sonication at 20,000 Hz at 100 watts of power for 1–2 minutes. The process was repeated and the protein concentration of the resulting suspension was determined using the BCA protein assay kit available from The Pierce Chemical Company and comparing the readings to the mean of values obtained using controls of bovine serum albumin and ovalbumin standards. The process yielded 6 to 9 milligrams of protein per milliliter (Sowa, B. A., et al, *Veterinary Microbiology*, 27:351–369 (1991)).

As a result of the unique nature of *Brucella abortus*, cell envelopes prepared as described above consist only of outer membrane-peptidoglycan complex (Sowa, et al., *Vet. Microbio.* 27:351–369, 1991). For the purpose of this invention, the terms cell envelopes and outer membrane-peptidoglycan (OM-PG) are used interchangeably.

4. Standardization and Determination of Amounts

Protein content of cell envelope preparations of *B. abortus* 2308 M106 was determined by the Pierce Chemical Company bicinchoninic acid (BCA) protein assay (Smith, P. K. et al. Measurement of Protein Using Bicinchoninic Acid, *Analytical Biochemistry*, 150:76–85 1985).

5. Unit assembly a. Assembly of Units to Make Serial

The adjuvant solution was homogenized with the cell envelopes such that 1.0 ml of the adjuvant solution contained the quantities for each immunogen as given in Table 1 (below), and 10 mls of the emulsion was dispensed into single 10 ml crimped, rubber stoppered vaccine vials. Each dose was 1 ml and each vial contained ten one ml doses.

b. Other Information

The sterility of the water solution and adjuvant material was determined by inoculation of 0.2 ml of the respective solutions onto 2% bovine blood nutrient agar plates and brucella agar nutrient agar with 5% bovine serum supplement and incubating for at least 5 days at 37° C.

6. Volume of Fill for Each Vial

The volume of fill for each vial was 10 mls.

7. Method and Technique of Filling and Sealing

The 10 ml of adjuvant/immunogen was dispensed by a multiple dose dispensing syringe and lyophilized with sealing and crimping done under vacuum.

The 10 mls of adjuvant/immunogen was dispensed by multi-dose dispensing syringe under a laminar flow hood and crimped and sealed with a rubber stopper.

8. Amount of Antigenic Material per Dose

The reconstituted cell envelopes of *B. abortus* Strain 2308 M106 contained 1,200.0 μg per 1.0 ml.

E. Testing

1. Potency

The immunogens were evaluated in cattle for their ability to induce significant protective immunity ($p<0.05$) at 240 days post vaccination by challenge with pathogenic $1\times10^7$ CFU *B. abortus* S 2308 described as follows.

Randomization of treatment groups was done by the following manner. A total of 76 heifers were available for assignment to 3 treatment groups. Ear tag numbers were assigned to these heifers. Since the cattle were "worked through the pens" in a random manner, the ear tags were assigned sequentially as they are handled. A random number generator was used to assign the 76 cows to 3 intermediate groups. The 3 treatments were assigned numbers from 1 to 3 and assigned to groups using a random number table.

The random numbers were selected in the following manner:

a. A disinterested individual selected the row and column to start with using the random number tables in *An Introduction to Statistical Methods and Data Analysis* by Ott, pg 713, Table 7.

The numbers (left to right) selected were: (53498, 18602 and 70659). Therefore treatment #5 was assigned to group #1 and treatment #3 was assigned to group #2 etc., until all treatments were assigned to a group.

Briefly, each heifer (at 130–200 days of gestation) was challenged by conjunctival instillation at 240 days post-vaccination with $10^7$ CFU of standard USDA virulent *B. abortus* Strain 2308 and monitored until 420 days post-vaccination for: (1) abortion, (2) *B. abortus* culture of each fetus, placental membranes, milk and 50 tissues from necropsy of each dam, and (3) monthly serology pre- and post-vaccination and weekly serology post-challenge to include the card test, Rivanol test, complement fixation (CF) test, and rough and smooth enzyme-linked immunosorbent assay (ELISA).

Data derived from the experiments were analyzed for the treatment groups described in Example III. For purposes of evaluation of the effects of vaccination treatments on protective immunity, the individual cattle from treatment groups was classified as not protected or protected.

Not protected heifers were defined as *B. abortus* Strain 2308 culture positive. Differences between treatments were evaluated by Fisher's Exact Test for discrete variables i.e. abortion, isolation, and seroreactivity.

EXAMPLE II

Assessement of the In Vitro and In Vivo Biologic Stability of M106 Transposon Mutant of *Brucella Abortus* for Use as Live Vaccines in Cattle This example clearly demonstrates the stability of the O-polysaccharide deficient transposon mutant m106. Thus, this transposon mutant is stable and its O-polysaccharide antigen deficient characteristic does NOT revert back to a smooth strain.

1. Introduction

The Brucellae are characterized by a number of phenotypic properties including colony type, antigenicity, virulence, growth rates, viability, resistance to antibiotics, and dye and salt sensitivity. Each of these characteristics has been found to vary individually but there is a high degree of association of changes in certain characteristics (Braun, W. Variation in the Genus Brucella. In *Symposium on Brucellosis*. AAAS, Washington. p. 26–36). The genetic basis for this variation (if any) is not known. M. Moriera Jacob found species and type reversion in 64 isolates out of a collection of 300 (Moriera-Jacob, M. 1963. In vitro species (or type) transformation among strains of Brucella. *Nature*. 197:406). Out of 35 isolates of *B. melitensis* stored for one year, 12 reverted to *B. intermedia*, 1 to *B. suis* and 3 to B. strain AM (*B. abortus* of M-serotype). Frequent identification of atypical isolates both in the United States and Canada have compelled some investigators to call for re-classification (Ewalt, D. R. and L. B. Forbes. 1987. Atypical isolates of *Brucella abortus* from Canada and the United States characterized as dye sensitive with M antigen dominant. *J. Clin. Microbiol*. 25:698–701).

Stability with regard to phenotypic variation is a relative term and depends upon the mechanism of variation. Variation may arise due to changes in growth conditions that alter gene expression. Such variation does not reflect true genotypic speciation. Taxonomic classification based on properties of this nature is fraught with difficulties as one tries to establish the properties which truly reflect species boundaries. This is especially true for the Brucella, the speciation and biotype analysis of which has depended on classification according to numerical analysis of phenotypic features. The phenotypic diversity of this group of organisms has lent itself to extensive analysis in an attempt to determine the taxonomic relationships. However, most researchers have concluded that the Brucella although generally divided into distinct forms nevertheless represent an almost infinite number of variants.

Point mutations occur naturally at a rate of $1\times10^{-6}$ per cell per generation and are easily revertible either at the primary site or by second site reversion. These also occur at a rate of $10^{-6}$. Deletions on the other hand do not revert at high frequency since the genetic information is lost. Reversion to wild type cannot occur without exchange of genetic information between cells or bacteriophage infection. Since exchange of this kind has not been documented for the Brucellae one may consider deletion mutants to be stable. In the case of transposon mutagenesis which occurs at a frequency of $10^{-2}$ to $10^{-3}$ reversion is observed at a well established level in the homologous system ($10^{-6}$ to $10^{-10}$ for wild type Tn5 in *E. coli* depending on the site of insertion). However, when introduced into a heterologous background, i.e., *E. coli* transposons introduced into *Brucella abortus*, it is difficult to predict the insertion and reversion frequency (Kleckner, N. 1981. Transposable elements in prokaryotes. *Ann. Rev. Genet*. 15: 341–404). Stability must therefore be determined empirically. A derivative of wild type Tn5 (Tn5 lac Z) was used in these experiments and has approximately 5% the transposition rate of wild type Tn5. The reversion rate would be expected to be correspondingly lower ($5\times10^{-8}$ to $5\times10^{-12}$).

2. Materials and General Methods

Three pregnant goats, #1, #2, #1985 were each vaccinated with $1\times10^9$ cells/ml of S19 vaccine (Positive Control), S2308 M106:Tn5 lacZ, and PBS (Negative Control) respectively.

Every week, the following samples were collected: swabs of faeces, urine, saliva, tears, and blood. The collection of samples was carried out for 22 weeks. Swabs were streaked in triplicate on Farrell's media plates supplemented with 100 IU/ml nystatin and 3 μm/ml cyclohexamide.

Blood sera were filtered through 0.45 μm and 0.22 μm filters consecutively, to decontaminate the sera. Blood sera were streaked on modified Farrell's media plates.

3. Results from Swab Analyses a. GOAT #1-S19 vaccine- Positive Control

*B. abortus* was not isolated from swabs of faeces, urine, saliva, tears, or blood.

b. GOAT #2-S2308::Tn5 lacZ (m106)

*B. abortus* was not isolated from swabs of faeces, urine, saliva, tears or blood.

c. GOAT #1985-Negative control

No *B. abortus* were isolated from swabs of faeces, urine, saliva, tears or blood.

4. Results from Necropsy Samples

Eight weeks post vaccination, Goat #1 parturated. Both mother and kid were necropsied. Twenty two weeks post vaccination, Goat #2, and #1985 had not conceived. Necropsy was carried out on both goats.

Gram-Stain and biotype analysis of colonies picked from all Farrell's plates were negative for *Brucella sp*.

No Brucella isolated from any tissue samples examined.

5. Serology Results

Goat #2, vaccinated with S2308::Tn5 lacZ m106, never developed antibodies against O-polysaccharide and was consistently brucella negative by card, rivanol, and complement fixation tests.

|  | Goat Number | | |
|---|---|---|---|
| (weeks) | 1 | 2 | 1985 |
| Bacteriology | | | |
| 0 | – | – | – |
| 1 | – | – | – |
| 2 | – | – | – |
| 3 | – | – | – |
| 4 | – | – | – |
| 5 | – | – | – |
| 20 | * | – | – |
| Card test | | | |
| 0 | – | – | – |
| 1 | + | – | – |
| 2 | + | – | – |
| 3 | + | – | – |
| 4 | + | – | – |
| 5 | – | – | – |
| 20 | * | – | – |
| Rivanol | | | |
| 0 | – | – | – |
| 1 | 400 | – | – |
| 2 | 400 | – | – |
| 3 | 400 | – | – |
| 4 | 400 | – | – |
| 5 | 200 | – | – |
| 6 | 100 | – | – |
| 7 | 100 | – | – |
| 8 | 200 | – | – |
| 20 | * | – | – |
| Complement fixation | | | |
| 0 | – | – | – |
| 1 | 1⁺40 | – | – |
| 2 | 2⁺20 | – | – |
| 3 | 3⁺20 | – | – |
| 4 | 3⁺20 | – | – |
| 5 | 2⁺20 | – | – |
| 6 | 2⁺10 | – | – |
| 7 | 1⁺10 | – | – |
| 8 | – | – | – |
| 20 | * | – | – |

-continued

| (weeks) | Goat Number | | |
|---|---|---|---|
| | 1 | 2 | 1985 |
| ELISA | | | |
| 0 | 0.140 | 0.139 | 0.209 |
| 1 | 0.726 | 0.179 | 0.207 |
| 2 | 1.28 | 0.168 | 0.370 |
| 3 | over | 0.156 | 0.420 |
| 4 | over | 0.124 | 0.374 |
| 5 | over | 0.164 | 0.286 |
| 6 | over | 0.134 | 0.278 |
| 7 | over | 0.210 | 0.254 |
| 8 | 1.157 | 0.137 | 0.272 |
| 9 | * | 0.140 | 0.150 |
| 10 | * | 0.102 | 0.164 |
| 11 | * | 0.086 | 0.180 |
| 12 | * | 0.199 | ND |
| 13 | * | 0.198 | 0.347 |
| 14 | * | 0.215 | 0.298 |
| 15 | * | 0.211 | 0.289 |
| 16 | * | 0.209 | 0.275 |
| 17 | * | 0.140 | 0.287 |
| 18 | * | 0.154 | 0.275 |
| 19 | * | 0.193 | 0.331 |
| 20 | * | 0.138 | 0.279 |

*sacrificed at week 8

6. Conclusions

Goats vaccinated with $1 \times 10^9$ cfu of transposon mutant S2308 M106::Tn5 had no organisms of the original phenotype (Km$^r$lac$^+$) recultured at any time post-exposure and no anti-O antibody was detected. By these criterion the results indicate that smooth organisms were undetectable either directly or indirectly. The reversion rate of m106 is therefore less than $3 \times 10^{-9}$ revertants/cfu. Thus, it is expected that reversion to smooth phenotype would not be observed under the conditions used to grow the organism and to vaccinate cattle, and for practical purposes the mutant may be considered stable.

The stability of these Km$^r$lacZ$^+$ strains in the absence of selection pressure was examined. Ten independent Km$^r$ of m106 transductants were streaked on Brucella agar plates without kanamycin. Single colonies from these plates were then grown in liquid shaker culture also in the absence of kanamycin at 37° C. for 30 generations (3–4 generations per liquid culture which was passaged 10 times). The cultures were plated on brucella agar and 100–500 colonies were replica plated onto Brucella agar. All colonies grew on both sets of plates. Thus kanamycin resistance was stable for at least 50 generations (20 generations from a single colony, 30 to 40 generations in liquid culture).

7. Summary

Transposon mutant m106 was found to be stable in that it does not revert to the smooth, O polysaccharide containing B. abortus strain. Transposon mutant m106 was not maintained in or excreted by goats. This mutant did not stimulate anti-LPS antibodies which could confuse diagnosis.

Transposon mutant m106 was found to be stable in that it did not revert to smooth, O polysaccharide containing B. abortus strain as evidenced by:

1) the lack of in vivo seroconversion in the goat experiment;
2) lack of survivability in goat tissues;
3) lack of detection of O polysaccharide by O polysaccharide specific monoclonal antibody when grown in liquid medium or solid medium; and
4) failure to revert even when passaged repeatedly in vitro, which favors spontaneous transposon excision.

EXAMPLE III

Summary of Studies of Cell Envelope Sub-Unit (Outer Membrane Peptidoglycan) Vaccines Against Bovine Brucellosis Using the Methods Described Above 1. Specific Aims Designed for the Evaluation of Killed Sub-Unit (Outer Membrane Peptidoglycan) Vaccines Against Bovine Brucellosis The purpose of developing and evaluating these killed sub-unit vaccine preparations against bovine brucellosis was to produce a safe and protective vaccine that:

i) does not stimulate antibodies cross-reactive with existing USDA standard serodiagnostic assays;
  ii) is not sex- or age-restricted, and;
  iii) is not infectious for man or animals, thereby eliminating undesirable side-effects of the current Strain 19 vaccine.

2. Test of Product Efficacy for Killed Sub-Unit (Outer Membrane Peptidoglycan) Vaccines Against Bovine Brucellosis Brucella abortus outer membrane peptidoglycan (OM-PG, Group 3) sub-unit vaccine preparations prepared as described above were compared to adjuvant alone (negative control, Group 1) and Strain 19 (positive control, Group 2) treatment groups of pregnant heifers in an approved statistically valid protocol as given in Table 1 below.

TABLE 1

| Experimental Groups | | | | | |
|---|---|---|---|---|---|
| Exp. Grp. | Immunogen | Dose of Brucella Antigens | | | No. of Cows* |
| | | Day 0*** | Day 57*** | Total | |
| 1 | Adjuvant** | none | none | none | 24 |
| 2 | Strain 19 | $3.4 \times 10^8$ | none | $3.4 \times 10^8$ | 20 |
| 3**** | M106 OM-PG | 1,200 µg | 1,200 µg | 2,400 µg | 16 |

*N = number of pregnant first calf heifers.
**0.25 mg monophosphoryl lipid A, 0.25 mg cell wall skeleton, 0.25 mg trehalose dimycolate, 0.1 ml Drakeol 6VR, 120 mg Lecithin, 0.004 ml monooleate (Tween 80).
***Volume of IM or SQ injection = 1.0 ml.
****M106 OM-PG plus adjuvant.

All cows were vaccinated on Week 0 (and Week 8 except for Strain 19 Group) and only pregnant cows were challenged on Week 37 with USDA standard virulent Brucella abortus S2308. The schedule of experimental procedures are as follows:

Blood samples for serum were collected from all cattle on Weeks −37, −27, −16 pre-vaccination, 0, 2, 4, 6, 8, 10, 13, 17, 21, 26, 30, 35, 37, 40, 41, 45, 47, 49, 51, 53, 55, and 57 post-vaccination. Cattle were injected with each treatment as given in Table 1 above (Group 1—adjuvant alone on Weeks 0 & 8, Group 2—Strain 19 only on Week 0, and Group 3—adjuvant plus m106 OM-PG on Weeks 0 and 8). All cattle were estrus synchronized with Synchromate B (Elanco) and bred naturally from Week 8 through Week 17 and challenged with $0.81 \times 10^7$ CFU virulent Strain 2308 at mid-gestation on Week 37 post-vaccination.

3. Results Obtained from the Evaluation of Killed Sub-Unit (Outer Membrane Peptidoglycan) Vaccines Against Bovine Brucellosis a. General Comments 1). Detailed Supporting Data Document Not Attached Herein Supporting data from all procedures, for all individual animals, for all treatment groups is available upon request.

2). Comparative Data For Group 1—Adjuvant Negative Control, Group 2—Strain 19 Positive Control, and Group 3 M106 OM-PG Results from treatment Group 1—Adjuvant="RADJ" (negative control), Group 2—Strain 19="S19" (positive control), and Group 3—M106 OM-PG="TN12×2" (derived from a transposon mutant of *Brucella abortus* Strain 2308) will be presented in this Example (see Table 28) below for statistical analysis).

b. Antibody Responses to Vaccination and Challenge

1. Methods Employed for this Study

The serological data obtained for each test is scored from "0" to "4" (see Table 2 for scoring of serologic results). Serologic results from Week 0 through Week +37 Post-Vaccination are graphed in the Tables 4–18.

Challenge with $0.81\times10^7$ cfu *Brucella abortus* S2308 occurred in Week +37. Abbreviations used in these Tables are as follows:

- VWK=Week pre- (−) or post- (+) vaccination;
- GPID=treatment group, i.e "RADJ"=Adjuvant Negative Control; "S19"=Strain 19 Positive Control; "TN12×2"=cell envelopes isolated from transposon mutant M106;
- UCF=complement fixation;
- UCD=card test;
- ELS=Smooth indirect Brucella ELISA;
- URV=Rivanol test; and
- ELR=Rough indirect Brucella ELISA.

Complete individual animal data, by treatment group and sequential experimental animal number are available upon request from Week −37 through Week +57.

TABLE 2

Criteria for Serologic Test Scoring Used in Graphs

| TEST | SCORE 0 | 1 | 2 | 3 | 4 |
|---|---|---|---|---|---|
| R-ELISA* | Neg | • | Doubtful | • | Pos |
| S-ELISA | Neg | • | Doubtful | • | Pos |
| CARD | Neg | • | • | • | Pos |
| CF** | 0 | 10 | 20 | 40 | 80+ |
| RIV** | 0 | 25 | 50 | 100 | 200+ |

*Neg = $OD_{405}$ ≦ 0.599, Doubtful = $OD_{405}$ ≧ 0.600 & ≦ 0.999, Pos = $OD_{405}$ < 1.000 • = time interval not scored
**Reciprocal titers Tables 3–7 present data obtained from "adjuvant only" (negative control, "RADJ," experimental group 1). The data are presented for each test (i.e. "ELR" is the rough indirect Brucella ELISA). Weeks 0, 2, 4, 6, 8, 10, 13, 17, 21, 26, 30, 35 and 37 are presented in these tables. Numbers underneath the scores are the number of animals studied (e.g. "25") and the percentage of the total is presented in the parenthesis ("(96.2)").

TABLE 3

TREAT: RADJ TEST: ELR

| Week | 0 | 2 | 4 | Total |
|---|---|---|---|---|
| 0 | 25 (96.2) | 1 (3.9) | 0 (0.0) | 26 |
| 2 | 21 (80.8) | 4 (15.4) | 1 (3.9) | 26 |

TABLE 3-continued

TREAT: RADJ TEST: ELR

| Week | 0 | 2 | 4 | Total |
|---|---|---|---|---|
| 4 | 16 (61.5) | 8 (30.8) | 2 (7.7) | 26 |
| 6 | 19 (73.1) | 4 (15.4) | 3 (11.5) | 26 |
| 8 | 25 (96.2) | 0 (0.0) | 1 (3.9) | 26 |
| 10 | 26 (100.0) | 0 (0.0) | 0 (0.0) | 26 |
| 13 | 26 (100.0) | 0 (0.0) | 0 (0.0) | 26 |
| 17 | 25 (96.2) | 1 (3.9) | 0 (0.0) | 26 |
| 21 | 25 (96.2) | 1 (3.9) | 0 (0.0) | 26 |
| 26 | 26 (100.0) | 0 (0.0) | 0 (0.0) | 26 |
| 30 | 26 (100.0) | 0 (0.0) | 0 (0.0) | 26 |
| 35 | 24 (100.0) | 0 (0.0) | 0 (0.0) | 24 |
| 37 | 23 (95.8) | 1 (4.2) | 0 (0.0) | 24 |

TABLE 4

TREAT: RADJ TEST: ELS

| Week | 0 | Total |
|---|---|---|
| 0 | 26 (100.0) | 26 |
| 2 | 26 (100.0) | 26 |
| 4 | 26 (100.0) | 26 |
| 6 | 26 (100.0) | 26 |
| 8 | 26 (100.0) | 26 |
| 10 | 26 (100.0) | 26 |
| 13 | 26 (100.0) | 26 |
| 17 | 26 (100.0) | 26 |
| 21 | 26 (100.0) | 26 |
| 26 | 26 (100.0) | 26 |
| 30 | 26 (100.0) | 26 |
| 35 | 24 (100.0) | 24 |
| 37 | 24 (100.0) | 24 |

TABLE 5

TREAT: RADJ TEST: UCD

| Week | 0 | Total |
|---|---|---|
| 0 | 26 (100.0) | 26 |
| 2 | 26 (100.0) | 26 |
| 4 | 26 (100.0) | 26 |
| 6 | 26 (100.0) | 26 |
| 8 | 26 (100.0) | 26 |
| 10 | 26 (100.0) | 26 |
| 13 | 26 (100.0) | 26 |
| 17 | 26 (100.0) | 26 |
| 21 | 26 (100.0) | 26 |
| 26 | 26 (100.0) | 26 |
| 30 | 26 (100.0) | 26 |
| 35 | 24 (100.0) | 24 |
| 37 | 24 (100.0) | 24 |

TABLE 6

TREAT: RADJ TEST: UCF

| Week | 0 | Total |
|---|---|---|
| 0 | 26 (100.0) | 26 |
| 2 | 26 (100.0) | 26 |
| 4 | 26 (100.0) | 26 |
| 6 | 26 (100.0) | 26 |
| 8 | 26 (100.0) | 26 |
| 10 | 26 (100.0) | 26 |
| 13 | 26 (100.0) | 26 |
| 17 | 24 (100.0) | 24 |
| 21 | 26 (100.0) | 26 |
| 26 | 26 (100.0) | 26 |

TABLE 6-continued

| | TREAT: RADJ | TEST: UCF | |
|---|---|---|---|
| Week | 0 | | Total |
| 30 | 26 (100.0) | | 26 |
| 35 | 24 (100.0) | | 24 |
| 37 | 24 (100.0) | | 24 |

TABLE 7

| | TREAT: RADJ | TEST: URV | |
|---|---|---|---|
| Week | 0 | | Total |
| 0 | 26 (100.0) | | 26 |
| 2 | 26 (100.0) | | 26 |
| 4 | 26 (100.0) | | 26 |
| 6 | 26 (100.0) | | 26 |
| 8 | 26 (100.0) | | 26 |
| 10 | 26 (100.0) | | 26 |
| 13 | 26 (100.0) | | 26 |
| 17 | 26 (100.0) | | 26 |
| 21 | 26 (100.0) | | 26 |
| 26 | 26 (100.0) | | 26 |
| 30 | 26 (100.0) | | 26 |
| 35 | 24 (100.0) | | 24 |
| 37 | 24 (100.0) | | 24 |

Tables 8–12 present data obtained from "Strain 19" as the immunogen (positive control, "S19," experimental group 2). The data are presented for each test (i.e. "ELR" is the rough indirect Brucella ELISA). One dose of $3.4 \times 10^8$ colony forming units was given on day 0 (see Table 1 above). Weeks 0, 2, 4, 6, 8, 10, 13, 17, 21, 26, 30, 35 and 37 are presented in these tables. Numbers underneath the scores are the number of animals studied (e.g. "25") and the percentage of the total is presented in the parenthesis ("(96.2)").

TABLE 8

| | TREAT: S19 | TEST: ELR | | |
|---|---|---|---|---|
| Week | 0 | 2 | 4 | Total |
| 0 | 24 (96.0) | 1 (4.0) | 0 (0.0) | 25 |
| 2 | 17 (68.0) | 8 (32.0) | 0 (0.0) | 25 |
| 4 | 8 (32.0) | 11 (44.0) | 6 (24.0) | 25 |
| 6 | 14 (56.0) | 6 (24.0) | 5 (20.0) | 25 |
| 8 | 21 (84.0) | 4 (16.0) | 0 (0.0) | 25 |
| 10 | 22 (88.0) | 3 (12.0) | 0 (0.0) | 25 |
| 13 | 25 (100.0) | 0 (0.0) | 0 (0.0) | 25 |
| 17 | 25 (100.0) | 0 (0.0) | 0 (0.0) | 25 |
| 21 | 20 (80.0) | 5 (20.0) | 0 (0.0) | 25 |
| 26 | 24 (96.0) | 1 (4.0) | 0 (0.0) | 25 |
| 30 | 22 (88.0) | 2 (8.0) | 1 (4.0) | 25 |
| 35 | 21 (100.0) | 0 (0.0) | 0 (0.0) | 21 |
| 37 | 20 (95.2) | 0 (0.0) | 1 (4.8) | 21 |

TABLE 9

| | TREAT: S19 | TEST: ELS | | |
|---|---|---|---|---|
| Week | 0 | 2 | 4 | Total |
| 0 | 25 (100.0) | 0 (0.0) | 0 (0.0) | 25 |
| 2 | 12 (48.0) | 13 (52.0) | 0 (0.0) | 25 |
| 4 | 2 (8.0) | 6 (24.0) | 17 (68.0) | 25 |
| 6 | 4 (16.0) | 10 (40.0) | 11 (44.0) | 25 |
| 8 | 8 (32.0) | 14 (56.0) | 3 (12.0) | 25 |
| 10 | 9 (36.0) | 12 (48.0) | 4 (16.0) | 25 |
| 13 | 16 (64.0) | 8 (32.0) | 1 (4.0) | 25 |

TABLE 9-continued

| | TREAT: S19 | TEST: ELS | | |
|---|---|---|---|---|
| Week | 0 | 2 | 4 | Total |
| 17 | 24 (96.0) | 1 (4.0) | 0 (0.0) | 25 |
| 21 | 25 (100.0) | 0 (00.0) | 0 (0.0) | 25 |
| 26 | 25 (100.0) | 0 (0.0) | 0 (0.0) | 25 |
| 30 | 23 (92.0) | 2 (8.0) | 0 (0.0) | 25 |
| 35 | 21 (100.0) | 0 (0.0) | 0 (0.0) | 21 |
| 37 | 21 (100.0) | 0 (0.0) | 0 (0.0) | 21 |

TABLE 10

| | TREAT: S19 | TEST: UCD | |
|---|---|---|---|
| Week | 0 | 4 | Total |
| 0 | 25 (100.0) | 0 (0.0) | 25 |
| 2 | 0 (0.0) | 25 (100.0) | 25 |
| 4 | 1 (4.0) | 24 (96.0) | 25 |
| 6 | 1 (4.0) | 24 (96.0) | 25 |
| 8 | 5 (20.0) | 20 (80.0) | 25 |
| 10 | 4 (16.0) | 21 (84.0) | 25 |
| 13 | 14 (56.0) | 11 (44.0) | 25 |
| 17 | 21 (84.0) | 4 (16.0) | 25 |
| 21 | 23 (92.0) | 2 (8.0) | 25 |
| 26 | 25 (100.0) | 0 (0.0) | 25 |
| 30 | 24 (96.0) | 1 (4.0) | 25 |
| 35 | 21 (100.0) | 0 (0.0) | 21 |
| 37 | 20 (95.2) | 1 (4.8) | 21 |

TABLE 11

| | TREAT: S19 | | TEST: UCF | | |
|---|---|---|---|---|---|
| Week 0 | 1 | 2 | 3 | 4 | Total |
| 0 | 25 (100.0) | 0 (0.0) | 0 (0.0) | 0 (0.0) | 0 (0.0) | 25 |
| 2 | 0 (0.0) | 1 (4.2) | 3 (12.5) | 2 (8.3) | 18 (75.0) | 25 |
| 4 | 2 (8.0) | 1 (4.00) | 4 (16.0) | 11 (44.0) | 7 (28.0) | 25 |
| 6 | 5 (20.0) | 8 (32.0) | 11 (44.0) | 1 (4.0) | 0 (0.0) | 25 |
| 8 | 20 (80.0) | 3 (12.0) | 2 (8.0) | 0 (0.0) | 0 (0.0) | 25 |
| 10 | 22 (88.0) | 3 (12.0) | 0 (0.0) | 0 (0.0) | 9 (0.0) | 25 |
| 13 | 25 (100.0) | 0 (0.0) | 0 (0.0) | 0 (0.0) | 0 (0.0) | 25 |
| 17 | 24 (100.0) | 0 (0.0) | 0 (0.0) | 0 (0.0) | 0 (0.0) | 24 |
| 21 | 24 (96.00) | 1 (4.0) | 0 (0.0) | 0 (0.0) | 0 (0.0) | 25 |
| 26 | 25 (100.0) | 0 (0.0) | 0 (0.0) | 0 (0.0) | 0 (0.0) | 25 |
| 30 | 25 (100.0) | 0 (0.0) | 0 (0.0) | 0 (0.0) | 0 (0.0) | 25 |
| 35 | 21 (100.0) | 0 (0.0) | 0 (0.0) | 0 (0.0) | 0 (0.0) | 21 |
| 37 | 21 (100.0) | 0 (0.0) | 0 (0.0) | 0 (0.0) | 0 (0.0) | 21 |

TABLE 12

| | TREAT: S19 | | TEST: URV | | |
|---|---|---|---|---|---|
| Week 0 | 1 | 2 | 3 | 4 | Total |
| 0 | 25 (100.0) | 0 (0.0) | 0 (0.0) | 0 (0.0) | 0 (0.0) | 25 |
| 2 | 0 (0.0) | 2 (8.0) | 6 (24.0) | 1 (4.0) | 16 (64.0) | 25 |
| 4 | 2 (8.00) | 2 (8.0) | 5 (20.0) | 5 (20.0) | 11 (44.0) | 25 |
| 6 | 2 (8.00) | 4 (16.0) | 10 (40.0) | 5 (20.0) | 4 (16.0) | 25 |
| 8 | 7 (28.0) | 7 (28.0) | 7 (28.0) | 4 (16.0) | 0 (0.0) | 25 |
| 10 | 10 (40.0) | 10 (40.0) | 4 (16.0) | 1 (4.0) | 0 (0.0) | 25 |
| 13 | 20 (80.0) | 3 (12.0) | 2 (8.0) | 0 (0.0) | 0 (0.0) | 25 |
| 17 | 25 (100.0) | 0 (0.0) | 0 (0.0) | 0 (0.0) | 0 (0.0) | 25 |
| 21 | 25 (100.0) | 0 (0.0) | 0 (0.0) | 0 (0.0) | 0 (0.0) | 25 |
| 26 | 25 (100.0) | 0 (0.0) | 0 (0.0) | 0 (0.0) | 0 (0.0) | 25 |
| 30 | 25 (100.0) | 0 (0.0) | 0 (0.0) | 0 (0.0) | 0 (0.0) | 25 |
| 35 | 21 (100.0) | 0 (0.0) | 0 (0.0) | 0 (0.0) | 0 (0.0) | 21 |
| 37 | 21 (100.0) | 0 (0.0) | 0 (0.0) | 0 (0.0) | 0 (0.0) | 21 |

Tables 13–17 present data obtained from "TN12×2" as the immunogen (cell envelopes isolated from transposon mutant M106, "TN12×2," experimental group 3). The data are scored and presented for each test (i.e. "ELR" is the rough indirect Brucella ELISA). One dose of 1,200 µg was given on day 0 and another dose of 1,200 µg was given on day 57 for a total of 2,400 µg (see Table 1 above). Weeks 0, 2, 4, 6, 8, 10, 13, 17, 21, 26, 30, 35 and 37 are presented in these tables. Numbers underneath the scores are the number of animals studied (e.g. "25") and the percentage of the total is presented in the parenthesis ("(96.2)").

TABLE 13

TREAT: TN12x2    TEST: ELR

| Week | 0 | 2 | 4 | Total |
|---|---|---|---|---|
| 0 | 20 (80.0) | 4 (16.0) | 1 (4.0) | 25 |
| 2 | 1 (4.0) | 15 (60.0) | 9 (36.0) | 25 |
| 4 | 2 (8.0) | 7 (28.0) | 16 (64.0) | 25 |
| 6 | 0 (0.0) | 7 (28.0) | 18 (72.0) | 25 |
| 8 | 4 (16.0) | 6 (24.0) | 15 (60.0) | 25 |
| 10 | 0 (0.0) | 1 (4.0) | 24 (96.0) | 25 |
| 13 | 0 (0.0) | 0 (0.0) | 24 (100.0) | 26 |
| 17 | 0 (0.0) | 1 (4.2) | 23 (95.9) | 24 |
| 21 | 0 (0.0) | 4 (16.7) | 20 (83.3) | 24 |
| 26 | 1 (4.35) | 6 (26.1) | 16 (69.6) | 23 |
| 30 | 2 (8.70) | 4 (17.4) | 17 (73.9) | 23 |
| 35 | 4 (25.0) | 5 (31.3) | 7 (43.8) | 16 |
| 37 | 1 (6.3) | 5 (31.3) | 10 (62.5) | 16 |

TABLE 14

TREAT: TN12x2    TEST: ELS

| Week | 0 | 2 | 4 | Total |
|---|---|---|---|---|
| 0 | 25 (100.0) | 0 (0.0) | 0 (00) | 25 |
| 2 | 22 (88.0) | 2 (8.0) | 1 (4.0) | 25 |
| 4 | 23 (92.0) | 2 (8.0) | 0 (0.0) | 25 |
| 6 | 25 (100.0) | 0 (0.0) | 0 (0.0) | 25 |
| 8 | 25 (100.0) | 0 (0.0) | 0 (0.0) | 25 |
| 10 | 20 (80.0) | 3 (12.0) | 2 (8.0) | 25 |
| 13 | 19 (79.2) | 4 (16.7) | 1 (4.2) | 24 |
| 17 | 23 (95.8) | 0 (0.0) | 1 (4.2) | 24 |
| 21 | 23 (95.8) | 1 (4.2) | 0 (0.0) | 24 |
| 26 | 22 (95.7) | 1 (4.4) | 0 (0.0) | 23 |
| 30 | 22 (95.7) | 1 (4.4) | 0 (0.0) | 23 |
| 35 | 16 (100.0) | 0 (0.0) | 0 (0.0) | 16 |
| 37 | 16 (100.0) | 0 (0.0) | 0 (0.0) | 16 |

TABLE 15

TREAT: TN12x2    TEST: UCD

| Week | 0 | 4 | Total |
|---|---|---|---|
| 0 | 25 (100.0) | 0 (0.0) | 25 |
| 2 | 25 (100.0) | 0 (0.0) | 25 |
| 4 | 25 (100.0) | 0 (0.0) | 25 |
| 6 | 25 (100.0) | 0 (0.0) | 25 |
| 8 | 25 (100.0) | 0 (0.0) | 25 |
| 10 | 24 (96.0) | 1 (4.0) | 25 |
| 13 | 24 (100.0) | 0 (0.0) | 24 |
| 17 | 24 (100.0) | 0 (0.0) | 24 |
| 21 | 24 (100.0) | 0 (0.0) | 24 |
| 26 | 23 (100.0) | 0 (0.0) | 23 |
| 30 | 23 (100.0) | 0 (0.0) | 23 |
| 35 | 16 (100.0) | 0 (0.0) | 16 |
| 37 | 16 (100.0) | 0 (0.0) | 16 |

TABLE 16

TREAT: TN12x2    TEST: UCF

| Week | 0 | 1 | 2 | 3 | Total |
|---|---|---|---|---|---|
| 0 | 25 (100.0) | 0 (0.0) | 0 (0.0) | 0 (0.0) | 25 |
| 2 | 25 (100.0 | 0 (0.0) | 0 (0.0) | 0 (0.0) | 25 |
| 4 | 25 (100.0) | 0 (0.0) | 0 (0.0) | 0 (0.0) | 25 |
| 6 | 25 (100.0) | 0 (0.0) | 0 (0.0) | 0 (0.0) | 25 |
| 8 | 25 (100.0) | 0 (0.0) | 0 (0.0) | 0 (0.0) | 25 |
| 10 | 23 (92.0) | 2 (8.0) | 0 (0.0) | 0 (0.0) | 25 |
| 13 | 24 (0.0) | 0 (0.0) | 0 (0.0) | 0 (0.0) | 24 |
| 17 | 22 (100.0) | 0 (0.0) | 0 (0.0) | 0 (0.0) | 22 |
| 21 | 24 (100.0) | 0 (0.0) | 0 (0.0) | 0 (0.0) | 24 |
| 26 | 22 (100.0) | 0 (0.0) | 0 (0.0) | 0 (0.0) | 22 |
| 30 | 23 (100.0) | 0 (0.0) | 0 (0.0) | 0 (0.0) | 23 |
| 35 | 16 (100.0) | 0 (0.0) | 0 (0.0) | 0 (0.0) | 16 |
| 37 | 16 (100.0) | 0 (0.0) | 0 (0.0) | 0 (0.0) | 16 |

TABLE 17

TREAT: TN12x2    TEST: URV

| Week | 0 | Total |
|---|---|---|
| 0 | 25 (100.0) | 25 |
| 2 | 25 (100.0) | 25 |
| 4 | 25 (100.0) | 25 |
| 6 | 25 (100.0) | 25 |
| 8 | 25 (100.0) | 25 |
| 10 | 25 (100.0) | 25 |
| 13 | 24 (100.0) | 24 |
| 17 | 24 (100.0) | 24 |
| 21 | 24 (100.0) | 24 |
| 26 | 23 (100.0) | 23 |
| 30 | 23 (100.0) | 23 |
| 35 | 16 (100.0) | 16 |
| 37 | 16 (100.0) | 16 |

2. Results of Antibody Responses

With the exception of one spurious card test and two complement fixation test results in Week 10, in treatment Group 3 (vaccinated with M106 OM-PG 1200 µg×2), no serologic responses were detected by the USDA standard card (Table 15), complement fixation (Table 16), or Rivanol (Table 17) diagnostic tests for brucellosis up to Week 37 (day of challenge) post-vaccination in the heifers vaccinated with the M106 OM-PG B. abortus vaccine. This demonstrated the virtual absence of cross-reactive antibodies which confuse standard USDA serodiagnostic tests. Good serologic responses predictive of protection as determined by the rough Brucella ELISA test occurred in all of the Group 3 sub-unit rough M106 OM-PG B. abortus vaccinated heifers (Table 13).

Additionally, Western Blot analyses using antibodies generated against the rough OM-PG sub-unit from B. abortus vaccinated cattle, corroborated the data obtained from the rough indirect Brucella ELISA test (serologic responses were observed in all of the Group 3 sub-unit rough M106 OM-PG B. abortus vaccinated heifers; data not given but available upon request).

In contrast to Group 3, Group 2 heifers vaccinated with Strain 19 had very high percentages of false positive serologic responses detected by the card (Table 10), complement fixation (Table 11) and rivanol (Table 12) tests beginning Week +2 post-vaccination. This group retained high diagnostic antibody titers through Week +37 post-vaccination.

Indeed, one cow (number 1269) was persistently infected with Strain 19, thus producing sustained high levels of antibodies detected by standard USDA serodiagnostic tests.

c. Cell Mediated Immune Responses

The cell mediated immune responses, as determined by peripheral blood lymphocyte transformation assays, are presented in Tables 18 and 19.

The results indicated that Group 3 heifers vaccinated with sub-unit M106 OM-PG B. abortus preparations responded as well as, if not better, than heifers vaccinated with Strain 19 when given two injections at a 2 month interval. The M106 OM-PG 1200 µg×2 vaccination regimen stimulated the greatest overall cell mediated immune response.

The data presented in Table 18 represent the in vitro lymphocyte responses of cattle to OM-PG antigen. These data clearly demonstrate that cattle vaccinated with strain M106 OM-PG had lymphocytes responsive to antigens contained in the OM-PG preparations. Significantly higher numbers of OM-PG vaccinated cows responded to OM-PG antigens than did cows given adjuvant alone or strain 19 vaccination. RB-51 is an O polysaccharide deficient mutant strain of B. abortus, Schurig et al. Biological properties of RB51; a stable rough strain of Brucella abortus. Vet. Microbiol., 28:171–188.

The data presented in Table 19 represent the in vitro lymphocyte responses of the same cattle to whole cell antigens of B. abortus strain 2308. These data also demonstrate significant numbers of responsive cattle in the groups that received of M106 OM-PG and in the group vaccinated with strain 19. For in vitro responses to these antigens, vaccination with strain 19 was statistically equivalent to vaccination with OM-PG.

The following conclusions are drawn from this cell mediated immune response data: (1) Lymphocyte responsiveness can be induced by OM-PG of rough strains of B. abortus and (2) The apparent specificity of lymphocytes responding to immunization with OM-PG differs from those responding to strain 19 vaccination.

A summary of the lymphocyte reactivities is presented below.

SUMMARY OF LYMPHOCYTE REACTIVITIES

| Cows Inoculated With: | Respond To: | |
|---|---|---|
| | Whole Cells | Rough OM-PG |
| Live Cells: Strain 19: Group 2 | Yes | Low |
| Rough OM-PG: Group 3 | Yes | Yes | d. Challenge & Bacteriologic Results

All pregnant cows were challenged with $0.81 \times 10^7$ cfu Brucella abortus S2308 in Week 37 and tissues and mammary secretions were collected at parturition and 30 days post-parturition if the first bacteriologic culture attempt was negative.

The results of bacteriologic cultures for recovery of Brucella abortus from the 11 composite tissues collected each cow and her corresponding fetus are given in Tables 20–27.

TABLE 18

FREQUENCY OF RESPONSES TO B. ABORTUS STRAIN RB51 OM-PG IN IMMUNIZED CATTLE

| Immunogen | Number of Positive Responses (Percent) | | | | | $\chi^2$ (P) versus Adj. | $\chi^2$ (P) versus Strain 19 | No. of Cows (Assays) |
|---|---|---|---|---|---|---|---|---|
| | None | 1 | 2 | 3 | 4 | | | |
| 1. Adjuvant | 21 (91) | 2 (9) | 0 (0.0) | 0 (0.0) | 0 (0.0) | na | na | 23 (84) |
| 2. Strain 19 | 9 (48) | 9 (33) | 2 (8) | 5 (21) | 0 (0.0) | 15.2* (0.002) | na | 24 (83) |
| 3. M106 OM-PG (2 × 1,200 µg) | 1 (4) | 6 (26) | 8 (35) | 6 (26) | 2 (9) | 36.2* (<0.001) | 12.4 (0.015) | 23 (87) |
| Total | 31 | 17 | 10 | 11 | 2 | | | 70 |

TABLE 19

FREQUENCY OF RESPONSES TO B. ABORTUS STRAIN 2308 IN IMMUNIZED CATTLE

| Immunogen | Number of Positive Responses (Percent) | | | | | $\chi^2$ (P) versus Adj. | $\chi^2$ (P) versus Strain 19 | No. of Cows (Assays) |
|---|---|---|---|---|---|---|---|---|
| | None | 1 | 2 | 3 | 4 | | | |
| 1. Adjuvant | 11 (48) | 8 (35) | 4 (17) | 0 (0) | 0 (0) | na | na | 23 (84) |
| 2. Strain 19 | 1 (4) | 7 (29) | 6 (25) | 9 (38) | 1 (4) | 18.9* (<0.001) | na | 24 (83) |
| 3. M106 OM-PG (2 × 1,200 µg) | 0 (0) | 6 (26) | 7 (30) | 6 (26) | 4 (17) | 22.0* (<0.001) | 3.7 (0.448) | 23 (87) |
| Total | 12 | 21 | 17 | 15 | 5 | | | 70 |

Data obtained from cows immunized with experimental groups 1–3 are presented in Tables 20–23. Data obtained from matching calfs from each cow are presented in Tables 24–27. Corresponding numbers followed by "A" represent the matching calf to the cow. Corresponding cow and calf tables are presented below. Conclusions from these challenge and bacteriologic studies are presented in Table 28. For example, table number 20 (cow) corresponds with table number 24 (calf), table 21 corresponds with table 25, table 22 corresponds with table 26 and table 23 corresponds with table 27.

The following abbreviations are used in these Tables: Gp. No.=experimental group number; Rec. Swab.=rectal swab; Med. LN=mediastinal lymph node; Lung=lung; Ab. Swab= abomasal swab; Abom.=abomasum; Placenta=placenta; Total=sum of each tissue; Dist.=number of culture positive tissues; Inf. Index=sum×total number of culture positive tissues; Average=sum divided by total number of culture positive tissues; Live Birth=calf that breathed (i.e. lungs were aerated).

TABLE 20

| Cow No. | Group No. | Pen No. | RF Milk | RR Milk | LF Milk | LR Milk | Vag. Sw. | Total | Dist. | Inf. Index | Average |
|---|---|---|---|---|---|---|---|---|---|---|---|
| 1218 | 1 | 5 | 0 | 0 | 0 | 0 | 0.0 | 0.0 | 0 | 0.0 | 0.00 |
| 1266 | 1 | 2 | 0 | 0 | 0 | 0 | 0.0 | 0.0 | 0 | 0.0 | 0.00 |
| 1273 | 1 | 2 | 0 | 0 | 0 | 0 | 0.0 | 0.0 | 0 | 0.0 | 0.00 |
| 1316 | 1 | 7 | 0 | 0 | 0 | 0 | 0.0 | 0.0 | 0 | 0.0 | 0.00 |
| 1410 | 1 | 4 | 0 | 0 | 0 | 0 | 0.0 | 0.0 | 0 | 0.0 | 0.00 |
| 1452 | 1 | 2 | 0 | 0 | 0 | 0 | 0.0 | 0.0 | 0 | 0.0 | 0.00 |
| 1454 | 1 | 8 | 0 | 0 | 0 | 0 | 0.0 | 0.0 | 0 | 0.0 | 0.00 |
| 1334 | 1 | 3 | 0 | 0 | 0 | 0 | 0.5 | 0.5 | 1 | 0.5 | 0.10 |
| 1283 | 1 | 2 | 0 | 0 | 0 | 0 | 1.0 | 1.0 | 1 | 1.0 | 0.20 |
| 1444 | 1 | 3 | 0 | 0 | 0 | 0 | 1.0 | 1.0 | 1 | 1.0 | 0.20 |
| 1326 | 1 | 5 | 0 | 0 | 0 | 0 | 2.5 | 2.5 | 1 | 2.5 | 0.50 |
| 1349 | 1 | 3 | 0 | 0 | 0 | 0 | 2.5 | 2.5 | 1 | 2.5 | 0.50 |
| 1229 | 1 | 7 | 0 | 0 | 0 | 1 | 0.5 | 1.5 | 2 | 3.0 | 0.30 |
| 1265 | 1 | 4 | 0 | 0 | 0 | 1 | 1.0 | 2.0 | 2 | 4.0 | 0.40 |
| 1318 | 1 | 3 | 1 | 1 | 0 | 0 | 1.0 | 3.0 | 3 | 9.0 | 0.60 |
| 1398 | 1 | 8 | 1 | 1 | 1 | 0 | 1.0 | 4.0 | 4 | 16.0 | 0.80 |
| 1399 | 1 | 4 | 1 | 1 | 1 | 1 | 0.0 | 4.0 | 4 | 16.0 | 0.80 |

TABLE 21

| Cow No. | Group No. | Pen No. | RF Milk | RR Milk | LF Milk | LR Milk | Vag. Sw. | Total | Dist. | Inf. Index | Average |
|---|---|---|---|---|---|---|---|---|---|---|---|
| 1268 | 1 | 4 | 0 | 1 | 1 | 0 | 4.0 | 6.0 | 3 | 18.0 | 1.20 |
| 1379 | 1 | 6 | 1 | 0 | 1 | 1 | 1.5 | 4.5 | 4 | 18.0 | 0.90 |
| 1321 | 1 | 5 | 1 | 2 | 0 | 2 | 4.5 | 9.5 | 4 | 38.0 | 1.90 |
| 1243 | 1 | 8 | 2 | 2 | 1 | 2 | 5.0 | 12.0 | 5 | 60.0 | 2.40 |
| 1217 | 1 | 6 | 2 | 2 | 1 | 3 | 4.5 | 12.5 | 5 | 62.5 | 2.50 |
| 1404 | 1 | 6 | 4 | 3 | 3 | 3 | 4.5 | 17.5 | 5 | 87.5 | 3.50 |
| 1220 | 1 | 7 | 3 | 4 | 4 | 3 | 5.0 | 19.0 | 5 | 95.0 | 3.80 |
| 1203 | 2 | 2 | 0 | 0 | 0 | 0 | 0.0 | 0.0 | 0 | 0.0 | 0.00 |
| 1248 | 2 | 7 | 0 | 0 | 0 | 0 | 0.0 | 0.0 | 0 | 0.0 | 0.00 |
| 1254 | 2 | 6 | 0 | 0 | 0 | 0 | 0.0 | 0.0 | 0 | 0.0 | 0.00 |
| 1269 | 2 | 2 | 0 | 0 | 0 | 0 | 0.0 | 0.0 | 0 | 0.0 | 0.00 |
| 1313 | 2 | 6 | 0 | 0 | 0 | 0 | 0.0 | 0.0 | 0 | 0.0 | 0.00 |
| 1322 | 2 | 7 | 0 | 0 | 0 | 0 | 0.0 | 0.0 | 0 | 0.0 | 0.00 |
| 1375 | 2 | 8 | 0 | 0 | 0 | 0 | 0.0 | 0.0 | 0 | 0.0 | 0.00 |
| 1390 | 2 | 4 | 0 | 0 | 0 | 0 | 0.0 | 0.0 | 0 | 0.0 | 0.00 |
| 1402 | 2 | 2 | 0 | 0 | 0 | 0 | 0.0 | 0.0 | 0 | 0.0 | 0.00 |
| 1427 | 2 | 5 | 0 | 0 | 0 | 0 | 0.0 | 0.0 | 0 | 0.0 | 0.00 |
| 1431 | 2 | 5 | 0 | 0 | 0 | 0 | 0.0 | 0.0 | 0 | 0.0 | 0.00 |

TABLE 22

| Cow No. | Group No. | Pen No. | RF Milk | RR Milk | LF Milk | LR Milk | Vag. Sw. | Total | Dist. | Inf. Index | Average |
|---|---|---|---|---|---|---|---|---|---|---|---|
| 1277 | 2 | 4 | 0 | 0 | 0 | 0 | 1.5 | 1.5 | 1 | 1.5 | 0.30 |
| 1237 | 2 | 5 | 0 | 3 | 0 | 0 | 0.0 | 3.0 | 1 | 3.0 | 0.60 |
| 1352 | 2 | 8 | 0 | 1 | 0 | 1 | 0.0 | 2.0 | 2 | 4.0 | 0.40 |
| 1314 | 2 | 8 | 1 | 2 | 0 | 1 | 0.0 | 4.0 | 3 | 12.0 | 0.80 |

TABLE 22-continued

| Cow No. | Group No. | Pen No. | RF Milk | RR Milk | LF Milk | LR Milk | Vag. Sw. | Total | Dist. | Inf. Index | Average |
|---|---|---|---|---|---|---|---|---|---|---|---|
| 1388 | 2 | 7 | 1 | 1 | 1 | 1 | 4.5 | 8.5 | 5 | 42.5 | 1.70 |
| 1394 | 2 | 4 | 2 | 2 | 1 | 1 | 4.0 | 10.0 | 5 | 50.0 | 2.00 |
| 1460 | 2 | 3 | 1 | 4 | 1 | 3 | 4.0 | 13.0 | 5 | 65.0 | 2.60 |
| 1270 | 2 | 6 | 4 | 5 | 1 | 2 | 4.5 | 16.5 | 5 | 82.5 | 3.30 |
| 1409 | 2 | 6 | 4 | 4 | 4 | 4 | 4.0 | 20.0 | 5 | 100.0 | 4.00 |
| 1353 | 3 | 4 | 0 | 0 | 0 | 0 | 0.5 | 0.5 | 1 | 0.5 | 0.10 |
| 1264 | 3 | 2 | 0 | 0 | 0 | 0 | 1.0 | 1.0 | 1 | 1.0 | 0.20 |
| 1389 | 3 | 4 | 0 | 0 | 0 | 0 | 1.0 | 1.0 | 1 | 1.0 | 0.20 |
| 1411 | 3 | 5 | 0 | 0 | 0 | 1 | 1.0 | 2.0 | 2 | 4.0 | 0.40 |
| 1299 | 3 | 5 | 1 | N.C. | 0 | 1 | 3.0 | 5.0 | 3 | 15.0 | 1.25 |
| 1339 | 3 | 7 | 1 | 1 | 0 | 1 | 2.5 | 5.5 | 4 | 22.0 | 1.10 |
| 1267 | 3 | 4 | 1 | 1 | 1 | 1 | 5.0 | 9.0 | 5 | 45.0 | 1.80 |
| 1295 | 3 | 5 | 1 | 1 | 2 | 3 | 2.0 | 9.0 | 5 | 45.0 | 1.80 |
| 1262 | 3 | 6 | 3 | 1 | 1 | 1 | 4.0 | 10.0 | 5 | 50.0 | 2.00 |

TABLE 23

| Cow No. | Group No. | Pen No. | RF Milk | RR Milk | LF Milk | LR Milk | Vag. Sw. | Total | Dist. | Inf. Index | Average |
|---|---|---|---|---|---|---|---|---|---|---|---|
| 1381 | 3 | 8 | 1 | 2 | 1 | 2 | 5.0 | 11.0 | 5 | 55.0 | 2.20 |
| 1397 | 3 | 6 | 1 | 3 | 1 | 3 | 4.0 | 12.0 | 5 | 60.0 | 2.40 |
| 1459 | 3 | 3 | 4 | 1 | 1 | 1 | 5.0 | 12.0 | 5 | 60.0 | 2.40 |
| 1225 | 3 | 8 | 2 | 3 | 2 | 1 | 4.5 | 12.5 | 5 | 62.5 | 2.50 |
| 1432 | 3 | 3 | 3 | 4 | 1 | 1 | 3.5 | 12.5 | 5 | 62.5 | 2.50 |
| 1293 | 3 | 7 | 4 | 3 | 1 | 2 | 4.5 | 14.5 | 5 | 72.5 | 2.90 |
| 1214 | 3 | 2 | 4 | 4 | 2 | 4 | 4.5 | 18.5 | 5 | 92.5 | 3.70 |

TABLE 24

| Calf No. | Gp. No. | Rec. Swab | Med. LN | Lung | Ab. Swab | Abom. | Placenta | Total | Dist. | Inf. Index | Average | Live Birth |
|---|---|---|---|---|---|---|---|---|---|---|---|---|
| 1218A | 1 | 1 | 0 | 0 | 0 | 0 | 0 | 1 | 1 | 1.0 | 0.17 | No |
| 1266A | 1 | 0 | 0 | 0 | 1 | 1 | 1 | 3 | 3 | 9.0 | 0.50 | Yes |
| 1273A | 1 | 5 | 4 | 5 | 5 | 0 | 3 | 22 | 5 | 110.0 | 3.67 | Yes |
| 1316A | 1 | 4 | 4 | 5 | 1 | 1 | 2 | 17 | 6 | 102.0 | 2.83 | No |
| 1410A | 1 | 0 | 0 | 0 | 0 | 0 | 0 | 0 | 0 | 0.0 | 0.00 | Yes |
| 1452A | 1 | 0 | 0 | 0 | 0 | 0 | 0 | 0 | 0 | 0.0 | 0.00 | No |
| 1454A | 1 | 0 | 1 | 1 | 0 | 0 | 0 | 2 | 2 | 4.0 | 0.33 | No |
| 1334A | 1 | 0 | 1 | 0 | 1 | 0 | 0 | 2 | 2 | 4.0 | 0.33 | Yes |
| 1283A | 1 | 4 | 4 | 4 | 0 | 1 | 1 | 14 | 5 | 70.0 | 2.33 | Yes |
| 1444A | 1 | 3 | 5 | 5 | 0 | 5 | 1 | 19 | 5 | 95.0 | 3.17 | No |
| 1326A | 1 | 1 | 0 | 0 | 0 | 0 | 4 | 5 | 2 | 10.0 | 0.83 | No |
| 1349A | 1 | 5 | 5 | 5 | 1 | 0 | 3 | 19 | 5 | 95.0 | 3.17 | Yes |
| 1229A | 1 | 1 | 1 | 5 | 0 | 0 | 1 | 8 | 4 | 32.0 | 1.33 | No |
| 1265A | 1 | 1 | 1 | 0 | 0 | 0 | 2 | 4 | 3 | 12.0 | 0.67 | Yes |
| 1318A | 1 | 1 | 0 | 5 | 0 | 4 | 1 | 11 | 4 | 44.0 | 1.83 | No |
| 1398A | 1 | 2 | 4 | 4 | 0 | 0 | 1 | 11 | 4 | 44.0 | 1.83 | No |
| 1399A | 1 | 0 | 0 | 0 | 0 | 0 | 0 | 0 | 0 | 0.0 | 0.00 | No |

TABLE 25

| Calf No. | Gp. No. | Rec. Swab | Med. LN | Lung | Ab. Swab | Abom. | Placenta | Total | Dist. | Inf. Index | Average | Live Birth |
|---|---|---|---|---|---|---|---|---|---|---|---|---|
| 1268A | 1 | 5 | 0 | 5 | 0 | 3 | 4 | 17 | 4 | 68.0 | 2.83 | Yes |
| 1379A | 1 | 0 | 1 | 0 | 1 | 1 | 1 | 4 | 4 | 16.0 | 0.67 | Yes |
| 1321A | 1 | 4 | 1 | 5 | 0 | 4 | 4 | 18 | 5 | 90.0 | 3.00 | No |
| 1243A | 1 | 3 | 2 | 4 | 4 | 3 | 5 | 21 | 6 | 126.0 | 3.50 | No |

TABLE 25-continued

| Calf No. | Gp. No. | Rec. Swab | Med. LN | Lung | Ab. Swab | Abom. | Placenta | Total | Dist. | Inf. Index | Average | Live Birth |
|---|---|---|---|---|---|---|---|---|---|---|---|---|
| 1217A | 1 | 4 | 5 | 5 | 1 | 3 | 4 | 22 | 6 | 132.0 | 3.67 | No |
| 1404A | 1 | 0 | 0 | 0 | 0 | 0 | 4 | 4 | 1 | 4.0 | 0.67 | Yes |
| 1220A | 1 | 0 | 1 | 0 | 0 | 0 | 4 | 5 | 2 | 10.0 | 0.83 | Yes |
| 1203A | 2 | 0 | 0 | 0 | 0 | 0 | 0 | 0 | 0 | 0.0 | 0.00 | No |
| 1248A | 2 | 0 | 0 | 0 | 0 | 0 | 0 | 0 | 0 | 0.0 | 0.00 | Yes |
| 1254A | 2 | 1 | 0 | 0 | 2 | 1 | 0 | 4 | 3 | 12.0 | 0.67 | Yes |
| 1269A | 2 | 0 | 0 | 0 | 0 | 0 | 0 | 0 | 0 | 0.0 | 0.00 | Yes |
| 1313A | 2 | 0 | 0 | 0 | 0 | 0 | 0 | 0 | 0 | 0.0 | 0.00 | Yes |
| 1322A | 2 | 0 | 1 | 1 | 0 | 0 | 0 | 2 | 2 | 4.0 | 0.33 | No |
| 1375A | 2 | 0 | 0 | 0 | 0 | 0 | 0 | 0 | 0 | 0.0 | 0.00 | Yes |
| 1390A | 2 | 5 | 3 | 4 | 2 | 0 | 2 | 16 | 5 | 80.0 | 2.67 | Yes |
| 1402A | 2 | 0 | 0 | 0 | 0 | 0 | 0 | 0 | 0 | 0.0 | 0.00 | Yes |
| 1427A | 2 | 0 | 0 | 0 | 1 | 0 | N.C. | 1 | 1 | 1.0 | 0.20 | Yes |
| 1431A | 2 | 0 | 0 | 0 | 0 | 0 | 0 | 0 | 0 | 0.0 | 0.00 | Yes |

TABLE 26

| Calf No. | Gp. No. | Rec. Swab | Med. LN | Lung | Ab. Swab | Abom. | Placenta | Total | Dist. | Inf. Index | Average | Live Birth |
|---|---|---|---|---|---|---|---|---|---|---|---|---|
| 1277A | 2 | 4 | 4 | 5 | 4 | 4 | 3 | 24 | 6 | 144.0 | 4.00 | No |
| 1237A | 2 | 0 | 0 | 0 | 0 | 0 | 0 | 0 | 0 | 0.0 | 0.00 | Yes |
| 1352A | 2 | 0 | 0 | 0 | 0 | 0 | 4 | 4 | 1 | 4.0 | 0.67 | Yes |
| 1314A | 2 | 0 | 0 | 0 | 0 | 0 | 0 | 0 | 0 | 0.0 | 0.00 | Yes |
| 1388A | 2 | 1 | 0 | 0 | 0 | 0 | 5 | 6 | 2 | 12.0 | 1.00 | Yes |
| 1394A | 2 | 0 | 0 | 3 | 0 | 0 | 5 | 8 | 2 | 16.0 | 1.33 | Yes |
| 1460A | 2 | 0 | 0 | 0 | 0 | 0 | 5 | 5 | 1 | 5.0 | 0.83 | Yes |
| 1270A | 2 | 1 | 0 | 1 | 0 | 0 | 5 | 7 | 3 | 21.0 | 1.17 | No |
| 1409A | 2 | 0 | 0 | 0 | 0 | 1 | 4 | 5 | 2 | 10.0 | 0.83 | Yes |
| 1353A | 3 | 0 | 0 | 0 | 0 | 0 | 1 | 1 | 1 | 1.0 | 0.17 | No |
| 1264A | 3 | 0 | 0 | 0 | 0 | 0 | 2 | 2 | 1 | 2.0 | 0.33 | YES |
| 1389A | 3 | 0 | 1 | 0 | 0 | 1 | 3 | 5 | 3 | 15.0 | 0.83 | Yes |
| 1411A | 3 | 0 | 0 | 0 | 0 | 0 | 0 | 0 | 0 | 0.0 | 0.00 | Yes |
| 1299A | 3 | 5 | 0 | 0 | 0 | 1 | 1 | 7 | 3 | 21.0 | 1.17 | Yes |
| 1339A | 3 | 4 | 3 | 5 | 1 | 2 | 5 | 20 | 6 | 120.0 | 3.33 | Yes |
| 1267A | 3 | 1 | 1 | 4 | 0 | 0 | 4 | 10 | 4 | 40.0 | 1.67 | Yes |
| 1295A | 3 | 4 | 1 | 3 | 0 | 0 | 4 | 12 | 4 | 48.0 | 2.00 | No |
| 1262A | 3 | 1 | 1 | 4 | 1 | 0 | 3 | 10 | 5 | 50.0 | 1.67 | Yes |

TABLE 27

| Calf No. | Gp. No. | Rec. Swab | Med. LN | Lung | Ab. Swab | Abom. | Placenta | Total | Dist. | Inf. Index | Average | Live Birth |
|---|---|---|---|---|---|---|---|---|---|---|---|---|
| 1381A | 3 | 1 | 0 | 0 | 0 | 0 | 4 | 5 | 2 | 10.0 | 0.83 | Yes |
| 1397A | 3 | 0 | 0 | 0 | 0 | 0 | 5 | 5 | 1 | 5.0 | 0.83 | Yes |
| 1459A | 3 | 0 | 0 | 1 | 0 | 0 | 5 | 6 | 2 | 12.0 | 1.00 | Yes |
| 1225A | 3 | 0 | 0 | 0 | 0 | 0 | 4 | 4 | 1 | 4.0 | 0.67 | Yes |
| 1432A | 3 | 0 | 0 | 0 | 0 | 0 | 5 | 5 | 1 | 5.0 | 0.83 | Yes |
| 1293A | 3 | 0 | 0 | 0 | 0 | 0 | 4 | 4 | 1 | 4.0 | 0.67 | Yes |
| 1214A | 3 | 2 | 2 | 1 | 0 | 1 | 5 | 11 | 5 | 55.0 | 1.83 | Yes | e. Protection Against Infection & Fetal Death

Using the data from the bacteriologic cultures and fetal death data, the results of the M106 OM-PG induced protection against infection and fetal death are given in the attached Table 28. The results were obtained when M106 OM-PG was injected at week 0 into heifers. These pregnant heifers (days of gestation at challenge=day 125 to day 185) were experimentally challenged on Week 37 Post-Vaccination with the USDA standard inoculum of $0.81 \times 10^7$ cfu B. abortus S2308.

The results from this study demonstrate that M106 OM-PG induced statistically significant ($p<0.001$) protection (87.5%) against fetal death, i.e. more living calves, as compared to non-vaccinated controls (45.8%). M106 OM-PG also stimulated more protective immunity against fetal death than did Strain 19 (80%), although not statistically significant. Neither Strain 19 ($p<0.057$) nor M106 OM-PG ($p<0.508$) produced statistically significant protection against infection as compared to non-vaccinated controls which reflects the severity of the experimental challenge. Additionally no statistical differences occurred when S19 was compared to M106 OM-PG with regard to protection against infection.

TABLE 28

Protection Against Infection and Fetal Death

| Group | N | Cow + Calf Culture Positive | Cow + Calf Culture Negative | % Protected | Fisher's Exact GP 1 vs. (p<) | Calfs§ Live | Calfs§ Dead | % Live | Fisher's Exact Gp 1 vs. (p<) |
|---|---|---|---|---|---|---|---|---|---|
| 1 | 24 | 22 | 2 | 11.0 | — | 11 | 13 | 45.8 | — |
| 2 | 20 | 13 | 7 | 33.3 | 0.057 NS | 16 | 4 | 80.0 | 0.030* |
| 3 | 16 | 16 | 0 | 0.0 | 0.508 NS | 14 | 2 | 87.5 | 0.001** |

§Without regard to fetal age at parturition.

None of the vaccines, including Strain 19, induced statistically significant protection against infection. However, both Group 2 (Strain 19) and Group 3 (M106 OM-PG 1200 µg×2) produced statistically significant protection against fetal death as compared to the Adjuvant negative control Group 1. No statistically significant differences were observed between the Strain 19 group and the M106 OM-PG vaccinated group.

M106 OM-PG vaccine, like Strain 19, greatly reduced the number of $B.\ abortus$ reaching the fetus as compared to the Adjuvant negative control Group 1 (data not shown). This reduction significantly increased fetal survivability while permitting an increasing number of $B.\ abortus$ to persist in the cow (data not shown). These data indicate that M106 OM-PG vaccinated cows would produce significantly more viable calves and shed fewer $B.\ abortus$ into the environment.

f. Safety and Toxicology Results

Intramuscular injections of the sub-unit rough (m106) cell envelope OM-PG $B.\ abortus$ vaccine into cattle produced detectable granulomas at 60 days after the first injection, as well as for 30 days after the second injection. Of interest, all granulomas spontaneously resolved 60 days after the second injection. These data are presented in Tables 29 and 30.

TABLE 29

Eight Week Post-First Vaccination
Intramuscular Injection Site Granulomas

| Group | Immunogen* | Granulomas (mm) Min | Max | Mean | S.D. | % Pos |
|---|---|---|---|---|---|---|
| 1 | Adjuvant | 0 | 0 | 0.0 | 0.0 | 0.0% |
| 2 | S19 | 0 | 0 | 0.0 | 0.0 | 0.0% |
| 3 | M106 OM-PG1200 × 1 | 0 | 34 | 15.9 | 10.5 | 76.0% |

*0.25 mg monophosphoryl lipid A, 0.25 mg cell wall skeleton, 0.25 mg trehalose dimycolate, 0.1 ml Drakeol 6VR, 0.004 ml monooleate (Tween 80), and 120 mg lecithin. Volume of IM or SQ injection = 1.0 ml.

TABLE 30

Four Week Post-Second Vaccination
Intramuscular Injection Site Granulomas

| Group | Immunogen* | Granulomas (mm) Min | Max | Mean | S.D. | % Pos |
|---|---|---|---|---|---|---|
| 1 | Adjuvant | 0 | 0 | 0.0 | 0.0 | 0.0% |

TABLE 30-continued

Four Week Post-Second Vaccination
Intramuscular Injection Site Granulomas

| Group | Immunogen* | Granulomas (mm) Min | Max | Mean | S.D. | % Pos |
|---|---|---|---|---|---|---|
| 2 | S19 | 0 | 0 | 0.0 | 0.0 | 0.0% |
| 3 | M106 OM-PG1200 × 2 | 0 | 24 | 4.0 | 8.0 | 17.0% |

*0.25 mg monophosphoryl lipid A, 0.25 mg cell wall skeleton, 0.25 mg trehalose dimycolate, 0.1 ml Drakeol 6VR, 0.004 ml monooleate (Tween 80), and 120 mg lecithin. Volume of IM or SQ injection = 1.0 ml.

g. Formulation and Pharmacy Results

The proportions and techniques for combining the purified rough OM-PG of *B. abortus* with the low oil adjuvant have been established using an USDA approved adjuvant formulation produced by Ribi Immunochem, Inc. under Good Laboratory Practices regulations. See above for details.

4. Summary of the Evaluation of Killed Sub-Unit (Outer Membrane Peptidoglycan) Vaccines Against Bovine Brucellosis The killed sub-unit rough M106 OM-PG *B. abortus* vaccine induced statistically significant ($p<0.001$) protection against fetal death, which was not significantly different from USDA Strain 19 vaccination (i.e. statistically equivalent).

The killed sub-unit OM-PG envelope vaccine did not stimulate significant cross reactivity on USDA card, Rivanol, or complement fixation diagnostic tests. This is in direct contrast to long term high levels of cross-reactive antibodies being stimulated by the standard USDA Strain 19 vaccine.

5. Conclusions Drawn from the Evaluation of Killed Sub-Unit (Outer Membrane Peptidoglycan) Vaccines Against Bovine Brucellosis The killed sub-unit rough M106 OM-PG *B. abortus* vaccine, like Strain 19, induced protection against fetal death for up to 37 weeks post-vaccination when inoculated as a two dose series at a 57 day interval. This protective immunity was obtained without stimulating cross reactive antibodies in standard USDA diagnostic assays.

Importantly, the use of M106 OM-PG *B. abortus* vaccine potentially means that any serologic responses detected by the current standard USDA serodiagnostic tests would indicate field strain infection, thus permitting protection and differential diagnosis.

EXAMPLE IV

Induced Protective Immunity With Live *B. Abortus* Transposon Mutant M106

In order to evaluate the protection induced by live M106 against brucellosis, a dose of $0.6 \times 10^{10}$ CFU of M106 was injected subcutaneously to vaccinate 25 cows as compared to 25 Strain 19 vaccinated positive control cows and 25 non-vaccinated negative control cows on Oct. 8, 1991. Serum samples were collected each 2 weeks for 6 weeks before vaccination and each 2 weeks since then to evaluate the immune response. These cows were estrus synchronized and bred naturally in preparation for virulent challenge with $1 \times 10^7$ CFU Strain 2308 on Week 37 post-vaccination. None of the cattle have developed brucellosis but they have demonstrated good antibody responses as detected by the rough indirect ELISA procedure.

From the above, it will be clear to one skilled in the art that several different approaches can be used to develop or to reach the same end result, namely a vaccine which provides protective immunity against *Brucella abortus*, yet provides a means for differentiating between field strain infected and vaccinated cattle.

What we claim is:

1. A vaccine for providing protective immunity against fetal death to a host animal against pathogenic *Brucella abortus* comprising cell envelopes isolated from *B. abortus* 2308 ml06 R::Tn5lacZ having ATCC Accession No. 67912, in an amount ranging from about 400 µg to about 4000 µg, together with a suitable carrier, wherein said cell envelopes have O polysaccharide antigen absent, wherein said *B. abortus* 2308 is killed by exposure to a $^{60}$Cobalt radiation at 4° C. wherein cell envelopes are isolated from said *B. abortus* 2308 and said suitable carrier is an adjuvant consisting essentially of 0.25 milligrams monophosphoryl lipid A, 0.25 milligrams Mycobacterium spp. cell wall skeleton, 0.25 milligrams of trehalose dimycolate 120 milligrams of lecithin, 0.1 milliliters DRAKEOL 6VR mineral oil, and 0.004 milliliters of TWEEN 80 monooleate detergent.

2. Isolated cell envelopes from *B. abortus* 2308 m106 R::Tn5 lacz having ATCC Accession Number 67912, wherein said cell envelopes have O polysaccharide antigen absent.

3. A vaccine for providing protective immunity against fetal death in a host animal against pathogenic *Brucella abortus* comprising *B. abortus* 2308 m106 R::Tn5lacZ having ATCC Accession No. 67912, in an mount ranging from about $10^9$ to about $10^{11}$ colony forming units.

4. *Brucella abortus* 2308 m 106 R::Tn5lacZ having ATCC Accession No. 67912.

5. The vaccine of claim 3 wherein said *B. abortus* 2308 is nonviable.

6. A vaccine for providing protective immunity against fetal death to a host animal against pathogenic *Brucella abortus* comprising cell envelopes isolated from the *B. abortus* 2308 of claim 4, in an amount ranging from about 400 µg to about 4000 µg, together with a suitable carrier, said cell envelopes have O polysaccharide antigen absent.

7. A vaccine for providing protective immunity in a host animal against pathogenic *Brucella abortus* comprising a stable, transposen mutant of *B. abortus* in an mount sufficient to induce protective immunity, wherein said transposen mutant comprises cell envelopes have O polysaccharide antigen absent.

* * * * *

UNITED STATES PATENT AND TRADEMARK OFFICE
CERTIFICATE OF CORRECTION

PATENT NO. : 5,718,903

DATED : FEBRUARY 17, 1998

INVENTORS : Leslie Garry Adams/Richard P. Crawford/Donald S. Davis/Thomas A. Ficht/ Roger Smith, III/Blair A. Sowa/Joe W. Templeton/John D. Williams/ Albert M. Wu It is certified that error appears in the above-identified patent and that said Letters Patent is hereby corrected as shown below:

In column 36, line 4, please insert a --,-- after "dimycolate".

In column 36, line 8, please delete "R::Tn5 lacz" and insert therefor --R::Tn5lacZ--.

In column 36, line 14, please delete "mount" and insert therefor --amount--.

In column 36, line 28, please delete "transposen" and insert therefor --transposon-- and delete "mount" and insert therefor --amount--.

In column 36, line 29, please delete "transposen" and insert therefor --transposon--.

Signed and Sealed this

Twelfth Day of May, 1998

*Attest:*

BRUCE LEHMAN

*Attesting Officer*  Commissioner of Patents and Trademarks